(12) United States Patent
Stupp et al.

(10) Patent No.: US 7,554,021 B2
(45) Date of Patent: Jun. 30, 2009

(54) COMPOSITION AND METHOD FOR SELF-ASSEMBLY AND MINERALIZATION OF PEPTIDE AMPHIPHILES

(75) Inventors: Samuel I. Stupp, Chicago, IL (US); Elia Beniash, Newton, MA (US); Jeffrey D. Hartgerink, Houston, TX (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 10/534,097

(22) PCT Filed: Nov. 12, 2003

(86) PCT No.: PCT/US03/35902

§ 371 (c)(1),
(2), (4) Date: Nov. 8, 2005

(87) PCT Pub. No.: WO2005/003292

PCT Pub. Date: Jan. 13, 2005

(65) Prior Publication Data

US 2006/0149036 A1 Jul. 6, 2006

Related U.S. Application Data

(60) Provisional application No. 60/425,536, filed on Nov. 12, 2002, provisional application No. 60/425,689, filed on Nov. 12, 2002.

(51) Int. Cl.
*B32B 15/00* (2006.01)
*A61K 38/00* (2006.01)

(52) U.S. Cl. .................... 977/705; 428/403; 428/843.7; 428/323; 428/327; 428/332; 428/636; 428/628; 428/40; 977/722; 530/350

(58) Field of Classification Search .................. 514/2
See application file for complete search history.

(56) References Cited

U.S. PATENT DOCUMENTS

| 4,554,101 A | 11/1985 | Hopp |
| 4,930,077 A | 5/1990 | Fan |
| 5,130,123 A | 7/1992 | Reynolds et al. |
| 5,208,111 A | 5/1993 | Decher et al. |
| 5,670,483 A | 9/1997 | Zhang et al. |
| 5,733,868 A | 3/1998 | Peterson et al. |
| 5,843,780 A | 12/1998 | Thomson |
| 5,871,767 A | 2/1999 | Dionne et al. |
| 5,955,343 A | 9/1999 | Holmes et al. |
| 5,993,541 A | 11/1999 | Litvin et al. |
| 6,051,272 A | 4/2000 | Stupp et al. |
| 6,085,206 A | 7/2000 | Domini et al. |
| 6,096,863 A | 8/2000 | Fields et al. |
| 6,156,321 A | 12/2000 | Thorpe et al. |
| 6,181,909 B1 | 1/2001 | Burstein et al. |
| 6,201,065 B1 | 3/2001 | Pathak et al. |
| 6,265,539 B1 | 7/2001 | Arlinghaus |
| 6,269,368 B1 | 7/2001 | Diamond |
| 6,270,765 B1 | 8/2001 | Deo et al. |
| 6,391,297 B1 | 5/2002 | Halvorsen |
| 6,444,723 B1 | 9/2002 | Kline |
| 6,458,924 B2 | 10/2002 | Knudsen et al. |
| 6,473,730 B1 | 10/2002 | McKeown et al. |
| 6,548,048 B1 | 4/2003 | Cuthbertson et al. |
| 6,548,630 B1 | 4/2003 | Zhang et al. |
| 6,562,619 B1 | 5/2003 | Gearhart et al. |

(Continued)

FOREIGN PATENT DOCUMENTS

JP 03099096 A 4/1991

(Continued)

OTHER PUBLICATIONS

Wong et al. (2000) Assembly of nanoparticles into hollow spheres using block copolypeptides, Nano Lett., vol. 2, No. 3, pp. 583-587.*
Slocik et al. (2002) Monoclonal antibody recognition of histidine-rich peptide encapsulated nanoclusters, Nano Lett., vol. 2, No. 3, pp. 169-173.*
Jin et al. (2001) Mechanism for the enhanced diffusion of charged oxygen ions in SiO2. Phys. Rev. Lett. vol. 86, No. 9, pp. 1793-1796.*
Shih et al. (2002) Two dimensional arrys of self-aseembled gold and sulfur-containing fullerene nanoparticles, Langmuir, vol. 18, pp. 3332-3335.*

(Continued)

*Primary Examiner*—Jon P Weber
*Assistant Examiner*—Samuel W Liu

(57) ABSTRACT

The present invention is directed to a composition useful for making homogeneously mineralized self assembled peptide-amphiphile nanofibers and nanofiber gels. The composition is generally a solution comprised of a positively or negatively charged peptide-amphiphile and a like signed ion from the mineral. Mixing this solution with a second solution containing a dissolved counter-ion of the mineral and/or a second oppositely charged peptide amphiphile, results in the rapid self assembly of the peptide-amphiphiles into a nanofiber gel and templated mineralization of the ions. Templated mineralization of the initially dissolved mineral cations and anions in the mixture occurs with preferential orientation of the mineral crystals along the fiber surfaces within the nanofiber gel. One advantage of the present invention is that it results in homogenous growth of the mineral throughout the nanofiber gel. Another advantage of the present invention is that the nanofiber gel formation and mineralization reactions occur in a single mixing step and under substantially neutral or physiological pH conditions. These homogeneous nanostructured composite materials are useful for medical applications especially the regeneration of damaged bone in mammals. This invention is directed to the synthesis of peptide-amphiphiles with more than one amphiphilic moment and to supramolecular compositions comprised of such multi-dimensional peptide-amphiphiles. Supramolecular compositions can be formed by self assembly of multi-dimensional peptide-amphiphiles by mixing them with a solution comprising a monovalent cation.

6 Claims, 5 Drawing Sheets

U.S. PATENT DOCUMENTS

| | | | |
|---|---|---|---|
| 6,800,481 | B1 | 10/2004 | Holmes et al. |
| 6,855,329 | B1 | 2/2005 | Shakesheff et al. |
| 6,890,654 | B2 | 5/2005 | Stupp et al. |
| 7,371,719 | B2 | 5/2008 | Stupp et al. |
| 7,390,526 | B2 | 6/2008 | Stupp et al. |
| 2002/0007217 | A1 | 1/2002 | Jacob et al. |
| 2002/0046018 | A1 | 4/2002 | Marcu et al. |
| 2002/0142277 | A1 | 10/2002 | Burstein et al. |
| 2002/0160471 | A1 | 10/2002 | Kisiday et al. |
| 2003/0059906 | A1 | 3/2003 | Hubbell et al. |
| 2003/0092672 | A1 | 5/2003 | Darcy et al. |
| 2003/0176335 | A1 | 9/2003 | Zhang et al. |
| 2004/0001893 | A1 | 1/2004 | Stupp et al. |
| 2004/0018961 | A1 | 1/2004 | Stupp et al. |
| 2004/0022718 | A1 | 2/2004 | Stupp et al. |
| 2004/0258726 | A1 | 12/2004 | Stupp et al. |
| 2005/0208589 | A1 | 9/2005 | Stupp et al. |
| 2005/0209145 | A1 | 9/2005 | Stupp et al. |
| 2005/0214257 | A1 | 9/2005 | Zhao et al. |
| 2005/0272662 | A1 | 12/2005 | Stupp et al. |
| 2006/0247165 | A1 | 11/2006 | Stupp et al. |

FOREIGN PATENT DOCUMENTS

| | | |
|---|---|---|
| WO | 93/22343 A1 | 11/1993 |
| WO | 94/02506 A1 | 2/1994 |
| WO | WO 97/14713 A1 | 4/1997 |
| WO | WO 97/20639 A1 | 6/1997 |
| WO | WO 98/07752 A1 | 2/1998 |
| WO | 99/36107 | 7/1999 |
| WO | 99/55383 A2 | 11/1999 |
| WO | WO 00/13710 A2 | 3/2000 |
| WO | 00/45831 A1 | 8/2000 |
| WO | WO 00/44808 A1 | 8/2000 |
| WO | WO 00/52145 A2 | 9/2000 |
| WO | WO 00/64481 A1 | 11/2000 |
| WO | WO 01/00650 A1 | 1/2001 |
| WO | WO 02/062969 A2 | 8/2002 |
| WO | WO 03/040336 A2 | 5/2003 |
| WO | WO 03/054146 A2 | 7/2003 |
| WO | WO 03/070749 A2 | 8/2003 |
| WO | WO 03/084980 A2 | 10/2003 |
| WO | WO 03/090255 A2 | 10/2003 |
| WO | WO 2004/003561 A1 | 1/2004 |
| WO | WO 2004/018628 A2 | 3/2004 |
| WO | WO 2004/024778 A2 | 3/2004 |
| WO | WO 2004/046167 A2 | 6/2004 |
| WO | WO 2004/072104 A2 | 8/2004 |
| WO | 2004/091370 A2 | 10/2004 |
| WO | WO 2004/106359 A2 | 12/2004 |
| WO | WO 2005/003292 A2 | 1/2005 |
| WO | 2005/014619 A2 | 2/2005 |
| WO | WO 2005/056039 A1 | 6/2005 |
| WO | WO 2005/056576 A2 | 6/2005 |
| WO | WO 2006/096614 A2 | 9/2006 |

OTHER PUBLICATIONS

Knake et al. (2005) Electrochemical nucleation of gold nanoparticles in a polymer film at a liquid-liquid interface, Langmuir, vol. 21, No. 3, pp. 1001-1008.*

Hartgerink et al., Self-Assembly and Mineralization of Peptide-Amphiphile Nanofibers, 2001, Science 294:1684-1688.

Aggeli et al., Responsive gels formed by the spontaneous self-assembly of peptides into polymeric β-sheet tapes, 1997, Nat., 259-262.

Holmes et al., 2000 (Reference to be provided at a later date).

Hartgerink et al., Peptide-amphiphile nanofibers: A versatile scaffold for the preparation of self-assembling materials, 2002, PNAS 99(8):5133-5138.

Zhang et al., 1995 (Reference to be provided at a later date).

Caplan et al., Self-Assembly of a β-Sheet Protein Governed by Relief of Electrostatic Repulsion Relative to van der Waals Attraction, 2000, Biomacromolecules 1:627-631.

Harris, 1991, #93 (Reference to be provided at a later date).

Isaac et al., Approaching Exponential Growth with a Self-Replicating Peptide, 2002, J. Am. Chem. Soc. 124:6808-6809.

Santoso et al., Structures, function and applications of amphiphilic peptides, 2002, Curr. Op. Colloid and Interface Sci. 7:262-266.

Busque et al., Progress toward a Peptidomimetic of Laminin-Derived Pentapeptide YIGSR: Synthesis of the Unique Tricyclic Core Structure, 2002, J. Org. Chem. 67:6097-6103.

Niece et al., Self-Assembly Combining Two Bioactive Peptide-Amphiphile Molecules into Nanofibers by Electrostatic Attraction, 2003, J. Am. Chem. Soc. 125:7146-7147.

Zhang, Fabrication of novel biomaterials through molecular self-assembly, 2003, Nature Biotech. 21(10):1171-1178.

Aizenberg, et al., Control of crystal nucleation by patterned self-assembly monolayers, 1999, Nature 398:495-498.

Braun et al., CdS Mineralization of Hexagonal, Lamellar, and Cubic Lyotropic Liquid Crystals, 1999, Mat. Res. Bull. 34(3):463-469.

Xu, Biomimetic Synthesis of Macroscopic-Scale Calcium Carbonate Thin Films. Evidence for a Multistep Assembly Process, 1998, J. Am. Chem. Soc. 120:11977-11985.

Murata et al., Membrane Fusion Induced by Mutual Interaction of the Two Charge-reversed Amphiphilic Peptides at Neutral pH, 1991, J. Biol. Chem. 266(22):14353-14358.

Yamada et al., Formation of Helical Super Structure from Single-Walled Bilayers by Amphiphiles with Oligo-L-Glutamic Acid-Head Group, 1984, Chemistry Letters, 10:1713-1716.

U.S. Appl. No. 11/337,316, filed Jan. 23, 2006, Stupp et al.

Brown, Walter E. Dec. 15, 1962. "Octacalcium Phosphate and Hydroxyapatite." *Nature*. vol. 196, pp. 1048-1050.

Liang, W. Y. and A. D. Yoffe. Jan. 8, 1968. "Transmission Spectra of ZnO Single Crystals." *Physical Review Letters*. vol. 20, No. 2, pp. 59-62.

Greenfield, Norma and Gerald D. Fasman. Oct. 1969. "Computed Circular Dichroism Spectra for the Evaluation of Protein Conformation." *Biochemistry*. vol. 8, No. 10, pp. 4108-4116.

Hantke, Klaus and Volkmar Braun. 1973. "Covalent Binding of Lipid to Protein: Diglyceride and Amide-Linked Fatty Acid at the N-Terminal End of the Murein-Lipoprotein of the *Escherichia coli* Outer Membrane." *Eur. J. Biochem*. vol. 34, No. 2, pp. 284-296.

Balcerski, James S., E: S. Pysh, G. M. Bonora, and C. Toniolo. Jun. 9, 1976. "Vacuum Ultraviolet Circular Dichroism of β-Forming Alkyl Oligopeptides." *Journal of the American Chemical Society*. vol. 98, No. 12, pp. 3470-3473.

Jacobson, Bruce S. and Daniel Branton. Jan. 21, 1977. "Plasma Membrane: Rapid Isolation and Exposure of the Cytoplasmic Surface by Use of Positively Charged Beads." *Science*. vol. 195, No. 4275, pp. 302-304.

Biesecker, G., J. Ieuan Harris, J. C. Thierry, J. E. Walker, and A. J. Wonacott. Mar. 24, 1977. *Nature*. vol. 266, pp. 328-333.

Kelly, Margaret M., E. S. Pysh, G. M. Bonora, and C. Toniolo. May 11, 1977. "Vacuum Ultraviolet Circular Dichroism of Protected Homooligomers Derived from L-Leucine." *Journal of the American Chemical Society*. vol. 99, No. 10, pp. 3264-3266.

Blumenthal, N. C., A. S. Posner, L. D. Silverman, and L. C. Rosenberg. 1979. "Effect of Proteoglycans on in Vitro Hydroxyapatite Formulation." *Calcified Tissue International*. vol. 27, No. 1, pp. 75-82.

Richardson, P. M., U. M. McGuinness, and A. J. Aguayo. Mar. 20, 1980. "Axons from CNS Neurones Regenerate into PNS Grafts." *Nature*. vol. 284, pp. 264-265.

Lim, Franklin and Anthony M. Sun. Nov. 21, 1980. "Microencapsulated Islets as Bioartificial Endocrine Pancreas." *Science*. vol. 210, No. 4472, pp. 908-910.

Jain, Rakesh K., Chhitar M. Gupta, and Nitya Anand. 1981. "Synthesis of Peptidylglycophospholipids, Novel Derivatives of Muramyl-Dipeptide." *Tetrahedron Letters*. vol. 22, No. 24, pp. 2317-2320.

Sarin, Virender K., Stephen B. H. Kent, James P. Tam, and R. B. Merrifield. 1981. "Quantitative Monitoring of Solid-Phase Peptide Synthesis by the Ninhydrin Reaction." *Analytical Biochemistry*. vol. 117, pp. 147-157.

Yannas, I. V., J. F. Burke, D. P. Orgill, E. M. Skrabut. Jan. 8, 1982. "Wound Tissue Can Utilize a Polymeric Template to Synthesize a Functional Extension of Skin." *Science*. vol. 215, No. 4529, pp. 174-176.

Montesano, R., L. Orci, and P. Vassalli. Nov. 1983. "In Vitro Rapid Organization of Endothelial Cells into Capillary-like Networks Is Promoted by Collagen Matrices." *The Journal of Cell Biology*. vol. 97, pp. 1648-1652.

Pierschbacher, Michael D. and Erkki Ruoslahti. May 3, 1984. "Cell Attachment Activity of Fibronectin Can Be Duplicated by Small Synthetic Fragments of the Molecule." *Nature*. vol. 309, pp. 30-33.

Landis, W. J. and J. R. Martin. Apr.-Jun. 1984. "X-Ray Photoelectron Spectroscopy Applied to Gold-Decorated Mineral Standards of Biological Interest." *J. Vac. Sci. Technol*. vol. A 2, No. 2, pp. 1108-1111.

Thompson, Nancy L., Adrienne A. Brian, and Harden M. McConnell. 1984. "Covalent Linkage of a Synthetic Peptide to a Fluorescent Phospholipid and Its Incorporation into Supported Phospholipid Monolayers." *Biochimica et Biophysica Acta*. vol. 772, pp. 10-19.

Addadi, L. and S. Weiner. Jun. 15, 1985. "Interactions Between Acidic Proteins and Crystals: Stereochemical Requirements in Biomineralization." *Proceedings of the National Academy of Sciences of the United States of America*. vol. 82, No. 12, pp. 4110-4114.

"Public Health Service Policy on Humane Care and Use of Laboratory Animals." Sep. 1986. Office for Protection from Research Risks (OPRR), National Institutes of Health.

Weiner, Stephen and Wolfie Traub. Oct. 1986. "Organization of Hydroxyapatite Crystals Within Collagen Fibrils." *FEBS Letters*. vol. 206, No. 2, pp. 262-266.

Mann, Stephen, John P. Hannington, and R. J. P. Williams. Dec. 11, 1986. "Phospholipid Vesicles as a Model System for Biomineralization." *Nature*. vol. 324, pp. 565-567.

Krimm, Samuel and Jagdeesh Bandekar. 1986. "Vibrational Spectroscopy and Conformation of Peptides, Polypeptides, and Proteins." *Advances in Protein Chemistry*. vol. 38, pp. 181-364.

de Groot, K., R. Geesink, C. P. A. T. Klein, and P. Serekian. Dec. 1987. "Plasma Sprayed Coatings of Hydroxylapatite." *Journal of Biomedical Materials Research*. vol. 21, No. 12, pp. 1375-1381.

Bresnahan, J. C., M. S. Beattie, F. D. Todd III, and D. H. Noyes. 1987. "A Behavorial and Anatomical Analysis of Spinal Cord Injury Produced by a Feedback-Controlled Impaction Device." *Experimental Neurology*. vol. 95, pp. 548-570.

Moscatelli, David. 1987. "High and Low Affinity Binding Sites for Basic Fibroblast Growth Factor on Cultured Cells: Absence of a Role for Low Affinity Binding in the Stimulation of Plasminogen Activator Production by Bovine Capillary Endothelial Cells." *Journal of Cellular Physiology*. vol. 131, pp. 123-130.

Lambert, Joseph B., Herbert F. Shurvell, David A. Lightner, and R. Graham Cooks. 1987. "Group Frequencies: Infrared and Raman." *Introduction to Organic Spectroscopy*. New York: Macmillan Publishing Company. pp. 169-182.

Cook, Stephen D., Kevin A. Thomas, John F. Kay, and Michael Jarcho. Jul. 1988. "Hydroxyapatite-Coated Titanium for Orthopedic Implant Applications." *Clinical Orthopaedics and Related Research*. No. 232, pp. 225-243.

Saksela, Olli, David Moscatelli, Andreas Sommer, and Daniel B. Rifkin. Aug. 1988. "Endothelial Cell-Derived Heparan Sulfate Binds Basic Fibroblast Growth Factor and Protects It from Proteolytic Degradation." *The Journal of Cell Biology*. vol. 107, pp. 743-751.

Cardin, Alan D. and H. J. R. Weintraub. Jan./Feb. 1989. "Molecular Modeling of Protein-Glycosaminoglycan Interactions." *Arteriosclerosis*. vol. 9, No. 1, pp. 21-32.

Oonishi, H., M. Yamamoto, H. Ishimaru, E. Tsuji, S. Kuskitani, M. Aono, and Y. Ukon. Mar. 1989. "The Effect of Hydroxyapatite Coating on Bone Growth into Porous Titanium Alloy Implants." *The Journal of Bone and Joint Surgery*. vol. 71-B, No. 2, pp. 213-216.

Friedmann, Theodore. Jun. 16, 1989. "Progress Toward Human Gene Therapy." *Science*. vol. 244, No. 4910, pp. 1275-1281.

Traub, Wolfie, Talmon Arad, and Stephen Weiner. Dec. 15, 1989. "Three-Dimensional Ordered Distribution of Crystals in Turkey Tendon Collagen Fibers." *Proceedings of the National Academy of Sciences of the United States of America*. vol. 86, No. 24, pp. 9822-9826.

Knorr, Reinhard, Arnold Trzeciak, Willi Bannwarth, and Dieter Gillessen. 1989. "New Coupling Reagents in Peptide Chemistry." *Tetrahedron Letters*. vol. 30, No. 15, pp. 1927-1930.

Sambrook, Joseph, Edward F. Fritsch, and Thomas Maniatis. 1989. "Genes Encoding Selectable Markers." *Molecular Cloning: A Laboratory Manual*. $2^{nd}$ ed. New York: Cold Spring Harbor Laboratory Press. pp. 16.9-16.15.

Veis, A. 1989. "Biochemical Studies of Vertebrate Tooth Mineralization." *Biomineralization*. S. Mann, J. Webb, and R. J. P. Williams, editors. Weinheim, Federal Republic of Germany: VCH Verlagsgesellschaft and New York: VCH Publishers. pp. 189-222.

Schnell, Lisa and Martin E. Schwab. Jan. 18, 1990. "Axonal Regeneration in the Rat Spinal Cord Produced by an Antibody Against Myelin-Associated Neurite Growth Inhibitors." *Nature*. vol. 343, pp. 269-272.

Ahn, Sang Tae and Thomas A. Mustoe. Jan. 1990. "Effects of Ischemia on Ulcer Wound Healing: A New Model in the Rabbit Ear." *Annals of Plastic Surgery*. vol. 24, No. 1, pp. 17-23.

Van de Pol, Frans C. M. Dec. 1990. "Thin-Flim ZnO—Properties and Applications." *Ceramic Bulletin*. vol. 69, No. 12, pp. 1959-1965.

Addadi, L., A. Berman, J. Moradian-Oldak, and S. Weiner. Dec. 28, 1990. "Tuning of Crystal Nucleation and Growth by Proteins: Molecular Interactions at Solid-Liquid Interfaces in Biomineralization." *Croatica Chemica Acta*. vol. 63, No. 3, pp. 539-544.

Sukenik, Chaim N., Natarajan Balachander, Lloyd A. Culp, Kristine Lewandowska, and Katherine Merritt. 1990. "Modulation of Cell Adhesion by Modification of Titanium Surfaces with Covalently Attached Self-Assembled Monolayers." *Journal of Biomedical Materials Research*. vol. 24, pp. 1307-1323.

Fields, C. G., D. H. Lloyd, R. L. Macdonald, K. M. Otteson, and R. L. Noble. Mar./Apr. 1991. "HBTU Activation for Automated Fmoc Solid-Phase Peptide Synthesis." *Peptide Research*. vol. 4, No. 2, pp. 95-101.

Harris, Robin, Editor. 1991. *Electron Microscopy in Biology: A Practical Approach*. New York: Oxford University Press.

Jackson, David Y., David S. King, Jean Chmielewski, Sunil Singh, and Peter G. Schultz. 1991. "General Approach to the Synthesis of Short α-Helical Peptides." *Journal of the American Chemical Society*. vol. 113, pp. 9391-9392.

Polverini, Peter J., Noel P. Bouck, and Farzan Rastinejad. 1991. "Assay and Purification of Naturally Occurring Inhibitor of Angiogenesis." *Methods in Enzymology*. vol. 198, pp. 440-450.

Weiner, Stephen and Wolfie Traub. Feb. 1992. "Bone Structure: From Ångstroms to Microns." *The FASEB Journal*. vol. 6, pp. 879-885.

Addadi, Lia and Stephen Weiner. 1992. "Control and Design Principles in Biological Mineralization." *Agnew. Chem. Int. Ed. Engl*. vol. 31, pp. 153-169.

Beresford, J. N., J. H. Bennett, C. Devlin, P. S. Leboy, and M. E. Owen. 1992. "Evidence for an Inverse Relationship Between the Differentiation of Adipocytic and Osteogenic Cells in Rat Marrow Stromal Cell Cultures." *Journal of Cell Science*. vol. 102, pp. 341-351.

Cook, Stephen D., Kevin A. Thomas, Jeanette E. Dalton, Todd K. Volkman, Thomas S. Whitecloud III, and John F. Kay. 1992. "Hydroxylapatite Coating of Porous Implants Improves Bone Ingrowth and Interface Attachment Strength." *Journal of Biomedical Materials Research*. vol. 26, pp. 989-1001.

Geahlen, Robert L., G. Marc Loudon, Lisa A. Paige, and David Lloyd. 1992. "A General Method for Preparation of Peptides Biotinylated at the Carboxy Terminus." *Analytical Biochemistry*. vol. 202, pp. 68-70.

Ghadiri, M. Reza, Christopher Soares, and Chong Choi. 1992. "Design of an Artificial Four-Helix Bundle Metalloprotein via a Novel Ruthenium(II)-Assisted Self-Assembly Process." *Journal of the American Chemical Society*. vol. 114, No. 10, pp. 4000-4002.

Kunitake, Toyoki. 1992. "Synthetic Bilayer Membranes: Molecular Design, Self-Organization, and Application." *Angew. Chem. Int. Ed. Engl*. vol. 31, pp. 709-726.

Stupp, Samuel I. and Glenn W. Ciegler. 1992. "Organoapatites: Materials for Artificial Bone. I. Synthesis and Microstructure." *Journal of Biomedical Materials Research*. vol. 26, pp. 169-183.

Surewicz, Witold K., Henry H. Mantsch, and Dennis Chapman. Jan. 19, 1993. "Determination of Protein Secondary Structure by Fourier Transform Infrared Spectroscopy: A Critical Assessment." *Biochemistry*. vol. 32, No. 2, pp. 389-394.

Zhang, Shuguang, Todd Holmes, Curtis Lockshin, and Alexander Rich. Apr. 15, 1993. "Spontaneous Assembly of a Self-Complementary Oligopeptide to Form a Stable Macroscopic Membrane." *Proceedings of the National Academy of Sciences of the United States of America*. vol. 90, No. 8, pp. 3334-3338.

Langer, Robert and Joseph P. Vacanti. May 14, 1993. "Tissue Engineering." *Science*. vol. 260, No. 5110, pp. 920-926.

Mulligan, Richard C. May 14, 1993. "The Basic Science of Gene Therapy." *Science*. vol. 260, No. 5110, pp. 926-932.

Massas, R., S. Pitaru, and M. M. Weinreb. Jun. 1993. "The Effects of Titanium and Hydroxyapatite on Osteoblastic Expression and Proliferation in Rat Parietal Bone Cultures." *Journal of Dental Research*. vol. 72, No. 6, pp. 1005-1008.

Archibald, Douglas D. and Stephen Mann. Jul. 29, 1993. "Template Mineralization of Self-Assembled Anisotropic Lipid Microstructures." *Nature*. vol. 364, pp. 430-433.

Atala, Anthony, Linda G. Cima, Wooseob Kim, Keith T. Paige, Joseph P. Vacanti, Alan B. Retik, and Charles A. Vacanti. Aug. 1993. "Injectable Alginate Seeded with Chondrocytes as a Potential Treatment for Vesicoureteral Reflux." *The Journal of Urology*. vol. 150, No. 2, pp. 745-747.

Ross-Murphy, S. B. and K. P. Shatwell. May-Aug. 1993. "Polysaccharide Strong and Weak Gels." *Biorheology*. vol. 30, Nos. 3 & 4, pp. 217-227.

Margalit, Hanah, Nurit Fischer, and Shmuel A. Ben-Sasson. Sep. 15, 1993. "Comparative Analysis of Structurally Defined Heparin Binding Sequences Reveals a Distinct Spatial Distribution of Basic Residues." *The Journal of Biological Chemistry*. vol. 268, No. 26, pp. 19228-19231.

Fowler, Bruce O., Milenko Marković, and Walter E. Brown. 1993. "Octacalcium Phosphate. 3. Infrared and Raman Vibrational Spectra." *Chem. Mater.* vol. 5, No. 10, pp. 1417-1423.

Fuhrhop, Jürgen-Hinrich, Dragan Spiroski, and Christoph Boettcher. 1993. "Molecular Monolayer Rods and Tubules Made of α-(L-Lysine),ω-(Amino) Bolaamphiphiles." *Journal of the American Chemical Society*. vol. 115, No. 4, pp. 1600-1601.

Graham, Stephan and Paul W. Brown. 1993. "The Low Temperature Formation of Octacalcium Phosphate." *Journal of Crystal Growth*. vol. 132, pp. 215-225.

Shimizu, Toshimi and Masakatsu Hato. 1993. "Self-Assembling Properties of Synthetic Peptidic Lipids." *Biochimica et Biophysica Acta*. vol. 1147, pp. 50-58.

Stupp, Samuel I., Jacqueline A. Hanson, Jo Ann Eurell, Glenn W. Ciegler, and Ann Johnson. 1993. "Organoapatites: Materials for Artifical Bone. III. Biological Testing." *Journal of Biomedical Materials Research*. vol. 27, pp. 301-311.

Stupp, Samuel I., George C. Mejicano, and Jacqueline A. Hanson. 1993. "Organoapatites: Materials for Artificial Bone. II. Hardening Reactions and Properties." *Journal of Biomedical Materials Research*. vol. 27, pp. 289-299.

Wald, Heidi L., Georgios Sarakinos, Michelle D. Lyman, Antonios G. Mikos, Joseph P. Vacanti, and Robert Langer. 1993. "Cell Seeding in Porous Transplantation Devices." *Biomaterials*. vol. 14, No. 4, pp. 270-278.

Walsh, Dominic, Joanne L. Kingston, Brigid R. Heywood, and Stephen Mann. 1993. "Influence of Monosaccharides and Related Molecules on the Morphology of Hydroxyapatite." *Journal of Crystal Growth*. vol. 133, pp. 1-12.

Wang, B. C., T. M. Lee, E. Chang, and C. Y. Yang. 1993. "The Shear Strength and the Failure Mode of Plasma-Sprayed Hydroxyapatite Coating to Bone: The Effect of Coating Thickness." *Journal of Biomedical Materials Research*. vol. 27, pp. 1315-1327.

San Antonio, James D., Arthus D. Lander, Morris J. Karnovsky, and Henry S. Slayter. Jun. 1994. "Mapping the Heparin-Binding Sites on Type I Collagen Monomers and Fibrils." *The Journal of Cell Biology*. vol. 125, No. 5, pp. 1179-1188.

Ban, S., S. Maruno, H. Iwata, and H. Itoh. 1994. "Calcium Phosphate Precipitation on the Surface of HA-G-Ti Composite Under Physiologic Conditions." *Journal of Biomedical Materials Research*. vol. 28, pp. 65-71.

de Bruijn, J. D., Y. P. Bovell, and C. A. van Blitterswijk. 1994. "Structural Arrangements at the Interface Between Plasma Sprayed Calcium Phosphates and Bone." *Biomaterials*. vol. 15, No. 7, pp. 543-550.

Hunter, Graeme K. and Harvey A. Goldberg. 1994. "Modulation of Crystal Formation by Bone Phosphoproteins: Role of Glutamic Acid-Rich Sequences in the Nucleation of Hydroxyapatite by Bone Sialoprotein." *Biochem. J.* vol. 302, pp. 175-179.

Klein, C. P. A. T., J. G. C. Wolke, J. M. A. de Blieck-Hogervorst, and K. de Groot. 1994. "Calcium Phosphate Plasma-Sprayed Coatings and Their Stability: An in Vivo Study." *Journal of Biomedical Materials Research*. vol. 28, pp. 909-917.

Mikos, Antonios G., Michelle D. Lyman, Lisa E. Freed, and Robert Langer. 1994. "Wetting of Poly(L-Lactic Acid) and Poly(DL-Lactic-co-glycolic Acid) Foams for Tissue Culture." *Biomaterials*. vol. 15, No. 1, pp. 55-58.

Bond, G. M., R. H. Richman, and W. P. McNaughton. Jun. 1995. "Mimicry of Natural Material Designs and Processes." *Journal of Materials Engineering and Performance*. vol. 4, No. 3, pp. 334-345.

Hubbell, Jeffrey A. Jun. 1995. "Biomaterials in Tissue Engineering." *Bio/technology*. vol. 13, pp. 565-576.

Fromm, J. R., R. E. Hilernan, E. E. O. Caldwell, J. M. Weiler, and R. J. Linhardt. Nov. 10, 1995. "Differences in the Interaction of Heparin with Arginine and Lysine and the Importance of these Basic Amino Acids in the Binding of Heparin to Acidic Fibroblast Growth Factor." *Archives of Biochemistry and Biophysics*. vol. 323, No. 2, pp. 279-287.

Wakitani, Shigeyuki, Tomoyuki Saito, and Arnold I. Caplan. Dec. 1995. "Myogenic Cells Derived from Rat Bone Marrow Mesenchymal Stem Cells Exposed to 5-Azacytidine." *Muscle & Nerve*. vol. 18, pp. 1417-1426.

Aletras, Alexios, Kleomenis Barlos, Dimitrios Gatos, Sophia Koutsogianni, and Petros Mamos. 1995. "Preparation of the Very Acid-Sensitive Fmoc-Lys(Mtt)-OH." *International Journal of Peptide & Protein Research*. vol. 45, pp. 488-496.

Berndt, Peter, Gregg B. Fields, and Matthew Tirrell. 1995. "Synthetic Lipidation of Peptides and Amino Acids: Monolayer Structure and Properties." *Journal of the American Chemical Society*. vol. 117, No. 37, pp. 9515-9522.

Gage, Fred H., Jasodhara Ray, and Lisa J. Fisher. 1995. "Isolation, Characterization, and Use of Stem Cells from the CNS." *Annual Review of Neuroscience*. vol. 18, pp. 159-192.

Nomizu, Motoyoshi, Benjamin S. Weeks, Christi A. Weston, Woo Hoo Kim, Hynda K. Kleinman, and Yoshihiko Yamada. 1995. "Structure-Activity Study of a Laminin α1 Chain Active Peptide Segment Ile-Lys-Val-Ala-Val (IKVAV)." *FEBS Letters*. vol. 365, pp. 227-231.

Saito, Tomoyuki, James E. Dennis, Donald P. Lennon, Randell G. Young, and Arnold I. Caplan. 1995. "Myogenic Expression of Mesenchymal Stem Cells Within Myotubes of *mdx* Mice in Vitro and in Vivo." *Tissue Engineering*. vol. 1, No. 4, pp. 327-343.

Sasanuma, Michio. 1995. "Optical Processes in ZnO." *J. Phys.: Condens. Matter*. vol. 7, pp. 10029-10036.

Zhang, Shuguang, Todd C. Holmes, C. Michael DiPersio, Richard O. Hynes, Xing Su, and Alexander Rich. 1995. "Self-Complementary Oligopeptide Matrices Support Mammalian Cell Attachment." *Biomaterials*. vol. 16, No. 18, pp. 1385-1393.

Falini, Guiseppe, Shira Albeck, Steve Weiner, and Lia Addadi. Jan. 5, 1996. "Control of Aragonite or Calcite Polymorphism by Mollusk Shell Macromolecules." *Science*. vol. 271, No. 5245, pp. 67-69.

Alivisatos, A. P. Feb. 16, 1996. "Semiconductor Clusters, Nanocrystals, and Quantum Dots." *Science*. vol. 271, No. 5251, pp. 933-937.

Keyt, Bruce A., Lea T. Berleau, Hung V. Nguyen, Helen Chen, Henry Heinsohn, Richard Vandlen, and Napoleone Ferrara. Mar. 29, 1996. "The Carboxyl-terminal Domain (111-165) of Vascular Endothelial Growth Factor Is Critical for Its Mitogenic Potency." *The Journal of Biological Chemistry*. vol. 271, No. 13, pp. 7788-7795.

Belcher, A. M., X. H. Wu, R. J. Christensen, P. K. Hansma, G. D. Stucky, and D. E. Morse. May 2, 1996. "Control of Crystal Phase Switching and Orientation by Soluble Mulluse-Shell Proteins." *Nature*. vol. 381, pp. 56-58.

Hortelano, Gonzalo, Ayman Al-Hendy, Frederick A. Ofosu, and Patricia L. Chang. Jun. 15, 1996. "Delivery of Human Factor IX in Mice by Encapsulated Recombinant Myoblasts: A Novel Approach Towards Allogenic Gene Therapy of Hemophilia B." *Blood*. vol. 87, No. 12, pp. 5095-5103.

Sultzbaugh, K. J. and T. J. Speaker. Jul.-Aug. 1996. "A Method to Attach Lectins to the Surface of Spermine Alginate Microcapsules Based on the Avidin Biotin Interaction." *J. Microencapsulation*. vol. 13, No. 4, pp. 363-375.

Alivisatos, A. Paul, Kai P. Johnsson, Xiaogang Peng, Troy E. Wilson, Colin J. Loweth, Marcel P. Burchez Jr., and Peter G. Schultz. Aug. 15, 1996. "Organization of 'Nanocrystal Molecules' Using DNA." *Nature*. vol. 382, pp. 609-611.

George, Anne, Leslie Bannon, Boris Sabsay, Jerry W. Dillon, James Malone, Arthur Veis, Nancy A. Jenkins, Debra J. Gilbert, and Neal G. Copeland. Dec. 20, 1996. "The Carboxyl-terminal Domain of Phosphophoryn Contains Unique Extended Triplet Amino Acid Repeat Sequences Forming Ordered Carboxyl-Phosphate Interaction Ridges That May Be Essential in the Biomineralization Process." *The Journal of Biological Chemistry*. vol. 271, No. 51, pp. 32869-32873.

Basso, D. Michele, Michael S. Beattie, and Jacqueline C. Bresnahan. 1996. "Graded Histological and Locomotor Outcomes after Spinal Cord Contusion Using the NYU Weight-Drop Device Versus Transection." *Experimental Neurology*. vol. 139, pp. 244-256.

Burkett, Sandra L. and Stephen Mann. 1996. "Spatial Organization and Patterning of Gold Nanoparticles on Self-Assembled Biolipid Tubular Templates." *Chem. Commun*. pp. 321-322.

Hunter, Graeme K., Peter V. Hauschka, A. Robin Poole, Lawrence C. Rosenberg, and Harvey A. Goldberg. 1996. "Nucleation and Inhibition of Hydroxyapatite Formation by Mineralized Tissue Proteins." *Biochem. J.* vol. 317, pp. 59-64.

Karymov, Mikhail A., Karel Procházka, John M. Mendenhall, Thomas J. Martin, Petr Munk, and Stephen E. Webber. 1996. "Chemical Attachment of Polystyrene-*block*-poly(methacrylic acid) Micelles on a Silicon Nitride Surface." *Langmuir*. vol. 12, No. 20, 4748-4753.

Landis, William J., Karen J. Hodgens. James Arena, Min Ja Song, and Bruce F. McEwen. 1996. "Structural Relations Between Collagen and Mineral in Bone as Determined by High Voltage Electron Microscopic Tomography." *Microscopy Research and Technique*. vol. 33, pp. 192-202.

Matsuzawa, Mieko, Forrest F. Weight, Richard S. Potember, and Päivi Liesi. 1996. "Directional Neurite Outgrowth and Axonal Differentiation of Embryonic Hippocampal Neurons Are Promoted by a Neurite Outgrowth Domain of the B2-Chain of Laminin." *Int. J. Devl. Neuroscience*. vol. 14, No. 3, pp. 283-295.

Mooney, David J., Daniel F. Baldwin, Nam P. Suh, Joseph P. Vacanti, and Robert Langer. 1996. "Novel Approach to Fabricate Porous Sponges of Poly(D,L-Lactic-co-glycolic Acid) Without the Use of Organic Solvents." *Biomaterials*. vol. 17, No. 14, pp. 1417-1422.

Ratner, Buddy D., Allan S. Hoffman, Frederick J. Schoen, and Jack E. Lemons, Editors. 1996. *Biomaterials Science: An Introduction to Materials in Medicine*. San Diego, CA: Academic Press.

Ulman, Abraham. 1996. "Formation and Structure of Self-Assembled Monolayers." *Chemical Reviews*. vol. 96, No. 4, pp. 1533-1554.

Yu, Ying-Ching, Peter Berndt, Matthew Tirrell, and Gregg B. Fields. 1996. "Self-Assembling Amphiphiles for Construction of Protein Molecular Architecture." *Journal of the American Chemical Society*. vol. 118, No. 50, pp. 12515-12520.

Zarif, Leila, Ange Polidori, Bernard Pucci, Tadek Gulik-Krzywicki, André A. Pavia, and Jean G. Riess. 1996. "Effect of Chirality on the Formation of Tubules from Glycolipidic Amphiphiles." *Chemistry and Physics of Lipids*. vol. 79, pp. 165-170.

Herr, Andrew B., David M. Ornitz, Ram Sasisekharan, Ganesh Venkataraman, and Gabriel Waksman. Jun. 27, 1997. "Heparin-Induced Self-Association of Fibroblast Growth Factor-2." *The Journal of Biological Chemistry*. vol. 272, No. 26, pp. 16382-16389.

Dimmeler, Stefanie and Andreas M. Zeiher. Aug. 1997. "Nitric Oxide and Apoptosis: Another Paradigm for the Double-Edged Role of Nitric Oxide." *Nitric Oxide: Biology and Chemistry*. vol. 1, No. 4, pp. 275-281.

Stupp, Samuel I. and Paul V. Braun. Aug. 29, 1997. "Molecular Manipulation of Microstructures: Biomaterials, Ceramics, and Semiconductors." *Science*. vol. 277, No. 5330, pp. 1242-1248.

Kaufmann, P. M., S. Heimrath, B. S. Kim, and D. J. Mooney. Sep./Oct. 1997. "Highly Porous Polymer Matrices as a Three-Dimensional Culture System for Hepatocytes." *Cell Transplantation*. vol. 6, No. 5, pp. 463-468.

Aggeli, Amalia, Mark Bell, Neville Boden, Jeff N. Keen, Tom C. B. McLeish, Irina Nyrkova, Sheena E. Radford, and Alexander Semenov. 1997. "Engineering of Peptide β-Sheet Nanotapes." *J. Mater. Chem.* vol. 7, No. 7, pp. 1135-1145.

Anderson, James M. and Matthew S. Shive. 1997. "Biodegradation and Biocompatibility of PLA and PLGA Microspheres." *Advanced Drug Delivery Reviews*. vol. 28, pp. 5-24.

Draget, Kurt Ingar, Gudmund Skjåk-Bræk, Olav Smidsrød. 1997. "Alginate Based New Materials." *International Journal of Biological Macromolecules*. vol. 21, pp. 47-55.

El-Ghannam, Ahmed, Paul Ducheyne, and Irving M. Shapiro. 1997. "Porous Bioactive Glass and Hydroxyapatite Ceramic Affect Bone Cell Function In Vitro Along Different Time Lines." *Journal of Biomedical Materials Research*. vol. 36, pp. 167-180.

Jaiswal, Neelam, Stephen E. Haynesworth, Arnold I. Caplan, and Scott P. Bruder. 1997. "Osteogenic Differentiation of Purified, Culture-Expanded Human Mesenchymal Stem Cells In Vitro." *Journal of Cellular Biochemistry*. vol. 64, pp. 295-312.

Nehrer, Stefan, Howard A. Breinan, Arun Ramappa, Sonya Shortkroff, Gretchen Young, Tom Minas, Clement B. Sledge, Ioannis V. Yannas, and Myron Spector. 1997. "Canine Chondrocytes Seeded in Type I and Type II Collagen Implants Investigated In Vitro." *Journal of Biomedical Materials Research (Appl. Biomater.)*. vol. 38, pp. 95-104.

Mann, Stephen. 1997. "Biomineralization: The Form(id)able Part of Bioinorganic Chemistry!" *J. Chem. Soc., Dalton Trans*. pp. 3953-3961.

Norrby, Klas. 1997. "Angiogenesis: New Aspects Relating to Its Initiation and Control." *APMIS*. vol. 105, pp. 417-437.

Shimizu, Toshimi, Masaki Kogiso, and Mitsutoshi Masuda. 1997. "Noncovalent Formation of Polyglycine II-Type Structure by Hexagonal Self-Assembly of Linear Polymolecular Chains." *Journal of the Americal Chemical Society*. vol. 119, No. 26, pp. 6209-6210, S2-S17.

Smith, George P. and Valery A. Petrenko. 1997. "Phage Display." *Chemical Reviews*. vol. 97, No. 2, pp. 391-410.

Toyotama, Akiko, Shin-ichi Kugimiya, Masakatsu Yonese, Takatoshi Kinoshita, and Yoshiharu Tsujita. 1997. "Controllable Orientation of the Peptide-Based Surfactant at Air-Water Interface." *Chemistry Letters*. pp. 443-444.

Weiner, Stephen and Lia Addadi. 1997. "Design Strategies in Mineralized Biological Materials." *J. Mater. Chem.* vol. 7, No. 5, pp. 689-702.

Wellings, Donald A. and Eric Atherton. 1997. "Standard Fmoc Protocols." *Methods in Enzymology*. vol. 289, pp. 44-67.

Wen, H. B., J. G. C. Wolke, J. R. de Wijn, Q. Liu, F. Z. Cui, and K. de Groot. 1997. "Fast Precipitation of Calcium Phosphate Layers on Titanium Induced by Simple Chemical Treatments." *Biomaterials*. vol. 18, No. 22, pp. 1471-1478.

Yu, Ying-Ching, Teika Pakalns, Yoav Dori, James B. McCarthy, Matthew Tirrell, and Gregg B. Fields. 1997. "Construction of Biologically Active Protein Molecular Architecture Using Self-Assembling Peptide-Amphiphiles." *Methods in Enzymology*. vol. 289, pp. 571-587.

Zhitomirsky, I. and L. Gal-Or. 1997. "Electrophoretic Deposition of Hydroxyapatite." *Journal of Materials Science: Materials in Medicine*. pp. 213-219.

Veis, Arthur, Kuiru Wei, Charles Sfeir, Anne George, and James Malone. Jan. 1998. "Properties of the $(DSS)_n$ Triplet Repeat Domain of Rat Dentin Phosphophoryn." *European Journal of Oral Sciences*. vol. 106 (suppl. 1), pp. 234-238.

Pincus, David W., Robert R. Goodman, Richard A. R. Fraser, Maiken Nedergaard, and Steven A. Goldman. Apr. 1998. "Neural Stem and Progenitor Cells: A Strategy for Gene Therapy and Brain Repair." *Neurosurgery*. vol. 42, No. 4, pp. 858-867.

Ogiso, M., Y. Yamashita, and T. Matsumoto. Jun. 1998. "The Process of Physical Weakening and Dissolution of the HA-Coated Implant in Bone and Soft Tissue." *Journal of Dental Research*. vol. 77, No. 6, pp. 1426-1434.

Petka, Wendy A., James L. Harden, Kevin P. McGrath, Denis Wirtz, and David A. Tirrell. Jul. 17, 1998. "Reversible Hydrogels from Self-Assembling Artificial Proteins." *Science*. vol. 281, No. 5375, pp. 389-392.

Orgill, Dennis P., Charles Butler, John F. Regan, Mark S. Barlow, I. V. Yannas, and Carolyn C. Compton. Aug. 1998. "Vascularized Collagen-Glycosaminoglycan Matrix Provides a Dermal Substrate and Improves Take of Cultured Epithelial Autografts." *Plastic and Reconstructive Surgery*. vol. 102, No. 2, pp. 423-429.

Yu, Ying-Ching, Matthew Tirrell, and Gregg B. Fields. Oct. 7, 1998. "Minimal Lipidation Stabilizes Protein-Like Molecular Architecture." *Journal of the American Chemical Society*. vol. 120, No. 39, pp. 9979-9987.

Borkenhagen, M., J.-F. Clémence, H. Sigrist, and P. Aebischer. 1998. "Three-Dimensional Extracellular Matrix Engineering in the Nervous System." *Journal of Biomedical Materials Research*. vol. 40, pp. 392-400.

Brekke, John H. and Jeffrey M. Toth. 1998. "Principles of Tissue Engineering Applied to Programmable Osteogenesis." *Journal of Biomedical Materials Research (Appl. Biomater.)*. vol. 43, pp. 380-398.

Fields, Gregg B., Janelle L. Lauer, Yoav Dori, Pilar Forns, Ying-Ching Yu, and Matthew Tirrell. 1998. "Proteinlike Molecular Architecture: Biomaterial Applications for Inducing Cellular Receptor Binding and Signal Transduction." *Biopolymers (Peptide Science)*. vol. 47, pp. 143-151.

Gu, Keni, Syweren R. Chang, Matt S. Slaven, Brian H. Clarkson, R. Bruce Rutherford, and Helena H. Ritchie. 1998. "Human Dentin Phosphophoryn Nucleotide and Amino Acid Sequence." *European Journal of Oral Sciences*. vol. 106, pp. 1043-1047.

Hartgerink, Jeffrey D., Thomas D. Clark, and M. Reza Ghadiri. 1998. "Peptide Nanotubes and Beyond." *Chem. Eur. J.* vol. 4, No. 8, pp. 1367-1372.

Johnstone, Brian, Thomas M. Hering, Arnold I. Caplan, Victor M. Goldberg, and Jung U. Yoo. 1998. "In Vitro Chondrogenesis of Bone Marrow-Derived Mesenchymal Progenitor Cells." *Experimental Cell Research*. vol. 238, pp. 265-272.

Kawasaki, M., A. Ohtomo, I. Ohkubo, H. Koinuma, Z. K. Tang, P. Yu, G. K. L. Wong, B. P. Zhang, and Y. Segawa. 1998. "Excitonic Ultraviolet Laser Emission at Room Temperature from Naturally Made Cavity in ZnO Nanocrytal Thin Films." *Materials Science and Engineering*. vol. B56, pp. 239-245.

Kogiso, Masaki, Satomi Ohnishi, Kiyoshi Yase, Mitsutoshi Masuda, and Toshimi Shimizu. 1998. "Dicarboxylic Oligopeptide Bolaamphiphiles: Proton-Triggered Self-Assembly of Microtubes with Loose Solid Surfaces." *Langmuir*. vol. 14, No. 18, pp. 4978-4986, S1-S7.

Kogiso, Masaki, Takeshi Hanada, Kiyoshi Yase, and Toshimi Shimizu. 1998. "Intralayer Hydrogen-Bond-Directed Self-Assembly of Nano-Fibers from Dicarboxylic Valyvaline Bolaamphiphiles." *Chem. Comm.* pp. 1791-1792.

Li, Panjian and Paul Ducheyne. 1998. "Quasi-Biological Apatite Film Induced by Titanium in a Simulated Body Fluid." *Journal of Biomedical Materials Research*. vol. 41, pp. 341-348.

Nanci, A., J. D. Wuest, L. Peru, P. Brunet, V. Sharma, S. Zalzal, and M. D. McKee. 1998. "Chemical Modification of Titanium Surfaces for Covalent Attachment of Biological Molecules." *Journal of Biomedical Materials Research*. vol. 40, pp. 324-335.

Tsui, Y. C., C. Doyle, and T. W. Clyne. 1998. "Plasma Sprayed Hydroxyapatite Coatings on Titanium Substrates Part 2: Optimisation of Coating Properites." *Biomaterials*. vol. 19, pp. 2031-2043.

Weiner, S. and H. D. Wagner. 1998. "The Material Bone: Structure-Mechanical Function Relations." *Annu. Rev. Mater. Sci.* vol. 28, pp. 271-298.

Wen, H. B., J. R. de Wijn, F. Z. Cui, and K. de Groot. 1998. "Preparation of Calcium Phosphate Coatings on Titanium Implant Materials by Simple Chemistry." *Journal of Biomedical Materials Research*. vol. 41, pp. 227-236.

Wheeler, Donna L., David L. Chamberland, John M. Schmitt, David C. Buck, John H. Brekke, Jeffrey O. Hollinger, S.-P. Joh, and K.-W. Suh. 1998. "Radiomorphometry and Biomedical Assessment of Recombinant Human Bone Morphogenetic Protein 2 and Polymer in Rabbit Radius Ostectomy Model." *Journal of Biomedical Materials Research (Appl. Biomater.)*. vol. 43, pp. 365-373.

Wolke, J. G. C., K. de Groot, and J. A. Jansen. 1998. "In Vivo Dissolution Behavior of Various RF Magnetron Sputtered Ca-P Coatings." *Journal of Biomedical Materials Research*. vol. 39, pp. 524-530.

Xiao, Shou-Jun, Marcus Textor, and Nicholas D. Spencer. 1998. "Covalent Attachment of Cell-Adhesive, (Arg-Gly-Asp)-Containing Peptides to Titanium Surfaces." *Langmuir*. vol. 14, No. 19, pp. 5507-5516.

Yamada, Norihiro, Katsuhiko Ariga, Masanobu Naito, Kazuhiro Matsubara, and Emiko Koyama. 1998. "Regulation of β-Sheet Structures Within Amyloid-Like β-Sheet Assemblage from Tripeptide Derivatives." *Journal of the American Chemical Society*. vol. 120, No. 47, pp. 12192-12199.

Chusuei, Charles C., D. Wayne Goodman, Michael J. Van Stipdonk, Dina R. Justes, and Emile A. Schweikert. Jan. 1, 1999. "Calcium Phosphate Phase Identification Using XPS and Time-of-Flight Cluster SIMS." *Analytical Chemistry*. vol. 71, No. 1, pp. 149-153.

Zubarev, Eugene R., Martin U. Pralle, Leiming Li, and Samuel I. Stupp. Jan. 22, 1999. "Conversion of Supramolecular Clusters to Macromolecular Objects." *Science*. vol. 283, pp. 523-526.

Won, You-Yeon, H. Ted Davis, and Frank S. Bates. Feb. 12, 1999. "Giant Wormlike Rubber Micelles." *Science*. vol. 283, No. 5404, pp. 960-963.

Corral, Claudio J., Aamir Siddiqui, Liancun Wu, Catherine L. Farrell, David Lyons, and Thomas A. Mustoe. Feb. 1999. "Vascular Endothelial Growth Factor Is More Important Than Basic Fibroblastic Growth Factor During Ischemic Wound Healing." *Arch. Surg.* vol. 134, pp. 200-205.

Wheeler, B. C., J. M. Corey, G. J. Brewer, and D. W. Branch. Feb. 1999. "Microcontact Printing for Precise Control of Nerve Cell Growth in Culture." *Journal of Biomechanical Engineering*. vol. 121, pp. 73-78.

Cao, H., Y. G. Zhao, S. T. Ho, E. W. Seelig, Q. H. Wang, and R. P. H. Chang. Mar. 15, 1999. "Random Laser Action in Semiconductor Powder." *Physical Review Letters*. vol. 82, No. 11, pp. 2278-2281.

Niklason, L. E., J. Gao, W. M. Abbott, K. K. Hirschi, S. Houser, R. Marini, and R. Langer. Apr. 16, 1999. "Functional Arteries Grown in Vitro." *Science*. vol. 284, pp. 489-493.

Hahn, Jungseok and Stephen E. Webber. Apr. 1999. "Modification of Surfaces by Covalent Attachment of Polymer Micelles." *Macromolecular Symposia*. vol. 139, pp. 39-47.

Liu, Yi, Duckhyun Kim, B. Timothy Himes, Stella Y. Chow, Timothy Schallert, Marion Murray, Alan Tessler, and Itzhak Fischer. Jun. 1, 1999. "Transplants of Fibroblasts Genetically Modified to Express BDNF Promote Regeneration of Adult Rat Rubrospinal Axons and Recovery of Forelimb Function." *The Journal of Neuroscience*. vol. 19, No. 11, pp. 4370-4387.

Mehler, Mark F. and John A. Kessler. Jul. 1999. "Progenitor Cell Biology: Implications for Neural Regeneration." *Arch. Neurol.* vol. 56, pp. 780-784.

Tirrell, M. Oct. 27, 1999. "Biofunctionalization of Surfaces with Peptide Amphiphiles." *AVS: Science & Technology*. Invited Paper BI-WeM7.

McDonald, John W., Xiao-Zhong Liu, Yun Qu, Su Liu, Shannon K. Mickey, Dorothy Turetsky, David I. Gottlieb, and Dennis W. Choi. Dec. 1999. "Transplanted Embryonic Stem Cells Survive, Differentiate and Promote Recovery in Injured Rat Spinal Cord." *Nature Medicine*. vol. 5, No. 12, pp. 1410-1412.

Bradt, Jens-Hilmar, Michael Mertig, Angelika Teresiak, and Wolfgang Pompe. 1999. "Biomimetic Mineralization of Collagen by Combined Fibril Assembly and Calcium Phosphate Formation." *Chem. Mater.* vol. 11, No. 10, pp. 2694-2701.

Butler, C. E., I. V. Yannas, C. C. Compton, C. A. Correia, and D. P. Orgill. 1999. "Comparison of Cultured and Uncultured Keratinocytes Seeded into a Collagen-GAG Matrix for Skin Replacements." *British Journal of Plastic Surgery.* vol. 52, pp. 127-132.

Chai, C. S. and B. Ben-Nissan. 1999. "Bioactive Nanocrystalline Sol-Gel Hydroxyapatite Coatings." *Journal of Materials Science: Materials in Medicine.* vol. 10, pp. 465-469.

Clark, Thomas D., Kenji Kobayashi, and M. Reza Ghadiri. 1999. "Covalent Capture and Stabilization of Cylindrical β-Sheet Peptide Assemblies." *Chem. Eur. J.* vol. 5, No. 2, pp. 782-792.

Cornish, J., K. E. Callon, C. Q.-X. Lin, C. L. Xiao, T. B. Mulvey, G. J. S. Cooper, and I. R. Reid. 1999. "Trifluoroacetate, a Contaminant in Purified Proteins, Inhibits Proliferation of Osteoblasts and Chondrocytes." *Am. J. Physiol. Endocrinol. Metab.* vol. 277, pp. 779-783.

Emoto, Kazunori, Yukio Nagasaki, and Kazunori Kataoka. 1999. "Coating of Surfaces with Stabilized Reactive Micelles from Poly-(ethylene glycol)—Poly(DL-Lactic Acid) Block Copolymer." *Langmuir.* vol. 15, No. 16, pp. 5212-5218.

Fields, Gregg B. 1999. "Induction of Protein-like Molecular Architecture by Self-Assembly Processes." *Bioorganic & Medicinal Chemistry.* vol. 7, pp. 75-81.

Haynes, Andrew J., Wei-Qun Huang, Jamie Mallah, Dajun Yang, Marc E. Lippman, and Lu-Yuan Li. 1999. "Angiopoietin-I and Its Receptor Tie-2 Participate in the Regulation of Capillary-like Tubule Formation and Survival of Endothelial Cells." *Microvascular Research.* vol. 58, pp. 224-237.

Hwang, Julia J., Kevin Jaeger, James Hancock, and Samuel I. Stupp. 1999. "Organoapatite Growth on an Orthopedic Alloy Surface." *Journal of Biomedical Materials Research.* vol. 47, pp. 504-515.

Ignjatović, Nenad, Simonida Tomić, Momčilo Dakić, Miroslav Miljković, Milenko Plavšić, and Dragan Uskoković. 1999. "Synthesis and Properties of Hydroxyapatite/Poly-L-Lactide Composite Biomaterials." *Biomaterials.* vol. 20, pp. 809-816.

Lee, Kevin J. and Thomas M. Jessell. 1999. "The Specification of Dorsal Cell Fates in the Vertebrate Central Nervous System." *Annual Review of Neuroscience.* vol. 22, pp. 261-294.

Lee, Kyujin C., Paul A. Carlson, Alex S. Goldstein, Paul Yager, and Michael H. Gelb. 1999. "Protection of a Decapeptide from Proteolytic Cleavage by Lipidation and Self-Assembly into High-Axial-Ratio Microstructures: A Kinetic and Structural Study." *Langmuir.* vol. 15, No. 17, pp. 5500-5508.

Mao, Chuanbin, Hengde Li, Fuzhai Cui, Chunlai Ma, and Qinglin Feng. 1999. "Oriented Growth of Phosphates on Polycrystalline Titanium in a Process Mimicking Biomineralization." *Journal of Crystal Growth.* vol. 206, pp. 308-321.

Miyaji, Fumiaki, Hyun-Min Kim, Shinichi Handa, Tadashi Kokubo, and Takashi Nakamura. 1999. "Bonelike Apatite Coating on Organic Polymers: Novel Nucleation Process Using Sodium Silicate Solution." *Biomaterials.* vol. 20, pp. 913-919.

Pakalns, Teika, Kraig L. Haverstick, Gregg B. Fields, James B. McCarthy, Daniel L. Mooradian, and Matthew Tirrell. 1999. "Cellular Recognition of Synthetic Peptide Amphiphiles is Self-Assembled Monolayer Films." *Biomaterials.* vol. 20, pp. 2265-2279.

Pittenger, Mark F., Alastair M. Mackay, Stephen C. Beck, Rama K. Jaiswal, Robin Douglas, Joseph D. Mosca, Mark A. Moorman, Donald W. Simonetti, Stewart Craig, and Daniel R. Marshak. Apr. 2, 1999. "Multilineage Potential of Adult Human Mesenchymal Stem Cells." *Science.* vol. 284, pp. 143-147.

Rezania, Alireza, Robert Johnson, Anthony R. Lefkow, and Kevin E. Healy. 1999. "Bioactivation of Metal Oxide Surfaces. 1. Surface Characterization and Cell Response." *Langmuir.* vol. 15, No. 20, pp. 6931-6939.

Rowley, Jon A., Gerard Madlambayan, and David J. Mooney. 1999. "Alginate Hydrogels as Synthetic Extracellular Matrix Materials." *Biomaterials.* vol. 20, pp. 45-53.

Schense, Jason C. and Jeffrey A. Hubbell. 1999. "Cross-Linking Exogenous Bifunctional Peptides into Fibrin Gels wtih Factor XIIIa." *Bioconjugate Chem.* vol. 10, No. 1, pp. 75-81.

Varma, H. K., Y. Yokogawa, F. F. Espinsoa, Y. Kawamoto, K. Nishizawa, F. Nagata, and T. Kameyama. 1999. "In-Vitro Calcium Phosphate Growth over Functionalized Cotton Fibers." *Journal of Materials Science: Materials in Medicine.* vol. 10, pp. 395-400.

Vernon, Robert B. and E. Helene Sage. 1999. "A Novel, Quantitative Model for Study of Endothelial Cell Migration and Sprout Formation Within Three-Dimensional Collagen Matrices." *Microvascular Research.* vol. 57, pp. 188-133.

Wei, M., A. J. Ruys, M. V. Swain, S. H. Kim, B. K. Milthorpe, and C. C. Sorrell. 1999. "Interfacial Bond Strength of Electrophoretically Deposited Hydroxyapatite Coatings on Metals." *Journal of Materials Science: Materials in Medicine.* vol. 10, pp. 401-409.

Yu, Ying-Ching, Vikram Roontga, Vladimir A. Daragan, Kevin H. Mayo, Matthew Tirrell, and Gregg B. Fields. 1999. "Structure and Dynamics of Peptide—Amphiphiles Incorporating Triple-Helical Proteinlike Molecular Architecture." *Biochemistry.* vol. 38, No. 5, pp. 1659-1668.

Huq, N. Laila, Keith J. Cross, and Eric C. Reynolds. Feb. 4, 2000. "Molecular Modelling of a Multiphosphorylated Sequence Motif Bound to Hydroxyapatite Surfaces." *Journal of Molecular Modeling.* vol. 6, pp. 35-47.

Martinez, J. S., G. P. Zhang, P. D. Holt, H.-T. Jung, C. J. Carrano, M. G. Haygood, and Alison Butler. Feb. 18, 2000. "Self-Assembling Amphiphilic Siderophores from Marine Bacteria." *Science.* vol. 287, No. 5456, pp. 1245-1247.

Verrecchio, Angela, Markus W. Germann, Barbara P. Schick, Brian Kung, Thomas Twardowski, and James D. San Antonio. Mar. 17, 2000. "Design of Peptides with High Affinities for Heparin and Endothelial Cell Proteoglycans." *The Journal of Biological Chemistry.* vol. 275, No. 11, pp. 7701-7707.

Cao, H., J. Y. Xu, E. W. Seelig, and R. P. H. Chang. May 22, 2000. "Microlaser Made of Disordered Media." *Applied Physics Letters.* vol. 76, No. 21, pp. 2997-2999.

Marler, Jennifer J., Amrita Guha, Jonathan Rowley, Rahul Koka, David Mooney, Joseph Upton, and Joseph Vacanti. May 2000. "Soft-Tissue Augmentation with Injectable Alginate and Syngeneic Fibroblasts." *Plastic and Reconstructive Surgery.* vol. 105, No. 6, pp. 2049-2058.

Holmes, Todd C., Sonsoles de Lacalle, Xing Su, Guosong Liu, Alexander Rich, and Shuguang Zhang. Jun. 6, 2000. "Extensive Neurite Outgrowth and Active Synapse Formation on Self-Assembling Peptide Scaffolds." *Proceedings of the National Academy of Sciences of the United States of America.* vol. 97, No. 12, pp. 6728-6733.

Whaley, Sandra R., D. S. English, Evelyn L. Hu, Paul F. Barbara, and Angela M. Belcher. Jun. 8, 2000. "Selection of Peptides with Semiconductor Binding Specificity for Directed Nanocrystal Assembly." *Nature.* vol. 405, pp. 665-668.

Sun, Xiu-xia and Chi-chen Wang. Jul. 28, 2000. "The N-Terminal Sequence (Residues 1-65) Is Essential for Dimerization, Activities, and Peptide Binding of *Escherichia coli* DsbC." *The Journal of Biological Chemistry.* vol. 275, No. 30, pp. 22743-22749.

Hsu, Wei-Cherng, Mark H. Spilker, Ioannis V. Yannas, and Peter A. D. Rubin. Aug. 2000. "Inhibition of Conjunctival Scarring and Contraction by a Porous Collagen-Glycosaminoglycan Implant." *Investigative Ophthalmology & Visual Science.* vol. 41, No. 9, pp. 2404-2411.

Schlessinger, Joseph, Alexander N. Plotnikov, Omar A. Ibrahimi, Anna V. Eliseenkova, Brian K. Yeh, Avner Yayon, Robert J. Linhardt, and Moosa Mohammadi. Sep. 2000. "Crystal Structure of a Ternary FGF-FGFR-Heparin Complex Reveals a Dual Role for Heparin in FGFR Binding and Dimerization." *Molecular Cell.* vol. 6, pp. 743-750.

Sun, Y., J. B. Ketterson, and G. K. L. Wong. Oct. 9, 2000. "Excitonic Gain and Stimulated Ultraviolet Emission in Nanocrystalline Zinc-Oxide Powder." *Applied Physics Letters.* vol. 77, No. 15, pp. 2322-2324.

Schuldiner, Maya, Ofra Yanuka, Joseph Itskovitz-Eldor, Douglas A. Melton, and Nissim Benvenisty. Oct. 10, 2000. "Effects of Eight Growth Factors on the Differentiation of Cells Derived from Human Embryonic Stem Cells." *Proceedings of the National Academy of Sciences of the United States of America.* vol. 97, No. 21, pp. 11307-11312.

Altman, Michael, Peter Lee, Alexander Rich, and Shuguang Zhang. 2000. "Conformational Behavior of Ionic Self-Complementary Peptides." *Protein Science.* vol. 9, pp. 1095-1105.

Archer, Eric A., Noah T. Goldberg, Vincent Lynch, and Michael J. Krische. 2000. "Nanostructured Polymer Duplexes via the Covalent Casting of 1-Dimensional H-Bonding Motifs: A New Strategy for the Self-Assembly of Macromolecular Precursors." *Journal of the American Chemical Society*. vol. 122. No. 20, pp. 5006-5007.

Ariga, Katsuhiko, Jun-ichi Kikuchi, Masanobu Naito, Emiko Koyama, and Norihiro Yamada. 2000. "Modulated Supramolecular Assemblies Composed of Tripeptide Derivatives: Formation of Micrometer-Scale Rods, Nanometer-Size Needles, and Regular Patterns with Molecular-Level Flatness from the Same Compound." *Langmuir*. vol. 16, No. 11, pp. 4929-4939.

Beniash, E., W. Traub, A. Veis, and S. Weiner. 2000. "A Transmission Electron Microscope Study Using Vitrified Ice Sections of Predentin: Structural Changes in the Dentin Collagenous Matrix Prior to Mineralization." *Journal of Structural Biology*. vol. 132, pp. 212-225.

Bigi, Adriana, Elisa Boanini, Silvia Panzavolta, and Norberto Roveri. 2000. "Biomimetic Growth of Hydroxyapatite on Gelatin Films Doped with Sodium Polyacrylate." *Biomacromolecules*. vol. 1, No. 4, pp. 752-756.

Bourel, Line, Olivier Carion, Hélène Gras-Masse, and Oleg Melnyk. 2000. "The Deprotection of Lys(Mtt) Revisited." *Journal of Peptide Science*. vol. 6, pp. 264-270.

Cardullo, F., M. Crego Calama, B. H. M. Snellink-Ruël, J.-L. Weidmann, A. Bielejewska, R. Fokkens, N. M. M. Nibbering, P. Timmerman, and D. N. Reinhoudt. 2000. "Covalent Capture of Dynamic Hydrogen-Bonded Assemblies." *Chem. Commun*. pp. 367-368.

Chamberlain, L. J., I. V. Yannas, H-P. Hsu, G. R. Strichartz, and M. Spector. 2000. "Near-Terminus Axonal Structure and Function Following Rat Sciatic Nerve Regeneration Through a Collagen-GAG Matrix in a Ten-Millimeter Gap." *Journal of Neuroscience Research*. vol. 60, pp. 666-677.

David, Sunil A., Satish K. Awasthi, and P. Balaram. 2000. "The Role of Polar and Facial Amphipathic Character in Determining Lipopolysaccharide-Binding Properties in Synthetic Cationic Peptides." *Journal of Endotoxin Research*. vol. 6, No. 3, pp. 249-256.

Dori, Yoav, Havazelet Bianco-Peled, Sushil K. Satija, Gregg B. Fields, James B. McCarthy, and Matthew Tirrell. 2000. "Ligand Accessibility as Means to Control Cell Response to Bioactive Bilayer Membranes." *Journal of Biomedical Materials Research*. vol. 50, pp. 75-81.

Forns, Pilar, Janelle L. Lauer-Fields, Su Gao, and Gregg B. Fields. 2000. "Induction of Protein-Like Molecular Architecture by Monoalkyl Hydrocarbon Chains." *Biopolymers*. vol. 54, pp. 531-546.

Hisaeda, Yoshio, Eiji Ohshima, and Makiko Arimura. 2000. "Aggregation Behavior of Synthetic Peptide Lipids with Arginine in Aqueous Solution and Construction of a Vitamin $B_{12}$ Artifical Enzyme." *Colloids and Surfaces A: Physicochemical and Engineering Aspects*. vol. 169, pp. 143-153.

Kogiso, Masaki, Yuji Okada, Takeshi Hanada, Kiyoshi Yase, and Toshimi Shimizu. 2000. "Self-Assembled Peptide Fibers from Valyvaline Bola-Amphiphiles by a Parallel β-Sheet Network." *Biochimica et Biophysica Acta*. vol. 1475, pp. 346-352.

Langer, Robert. 2000. "Biomaterials in Drug Delivery and Tissue Engineering: One Laboratory's Experience." *Accounts of Chemical Research*. vol. 33, No. 2, pp. 94-101.

Liu, X. D., M. Skold, T. Umino, Y. K. Zhu, D. J. Romberger, J. R. Spurzem, and S. I. Rennard. 2000. "Endothelial Cell-Mediated Type I Collagen Gel Contraction Is Regulated by Hemin." *J. Lab. Clin. Med*. vol. 136, No. 2, pp. 100-109.

Lu, Lichun, Susan J. Peter, Michelle D. Lyman, Hui-Lin Lai, Susan M. Leite, Janet A. Tamada, Shiro Uyama, Joseph P. Vacanti, Robert Langer, and Antonios G. Mikos. 2000. "In Vitro and in Vivo Degradation of Porous Poly(DL-Lactic-*co*-Glycolic Acid) Foams." *Biomaterials*. vol. 21, pp. 1837-1845.

Matsuura, T., R. Hosokawa, K. Okamoto, T. Kimoto, and Y. Akagawa. 2000. "Diverse Mechanisms of Osteoblast Spreading on Hydroxyapatite and Titanium." *Biomaterials*. vol. 21, pp. 1121-1127.

Ponticiello, Michael S., Robert M. Schinagl, Sudha Kadiyala, and Frank P. Barry. 2000. "Gelatin-Based Resorbable Sponge as a Carrier Matrix for Human Mesenchymal Stem Cells in Cartilage Regeneration Therapy." *Journal of Biomedical Materials Research*. vol. 52, pp. 246-255.

Powell, Sharon K., Jayashree Rao, Eva Roque, Motoyoshi Nomizu, Yuichiro Kuratomi, Yoshihiko Yamada, and Hynda K. Kleinman. 2000. "Neural Cell Response to Multiple Novel Sites on Laminin-1." *Journal of Neuroscience Research*. vol. 61, pp. 302-312.

Sakiyama-Elbert, Shelly E. and Jeffrey A. Hubbell. 2000. "Controlled Release of Nerve Growth Factor from a Heparin-Containing Fibrin-Based Cell Ingrowth Matrix." *Journal of Controlled Release*. vol. 69, pp. 149-158.

Sakiyama-Elbert, Shelly E. and Jeffrey A. Hubbell. 2000. "Development of Fibrin Derivatives for Controlled Release of Heparin-Binding Growth Factors." *Journal of Controlled Release*. vol. 65, pp. 389-402.

Thareja, R. K. and A. Mitra. 2000. "Random Laser Action in ZnO." *Appl. Phys*. vol. B 71, pp. 181-184.

Tunggal, Patrick, Neil Smyth, Mats Paulsson, and Mark-Christoph Ott. 2000. "Laminins: Structure and Genetic Regulation." *Microscopy Research and Technique*. vol. 51, pp. 214-227.

do Serro, Ana Paula Valagão Amadeu, Anabela Catarino Fernandes, and Benilde de Jesus Vieira Saramago. 2000. "Calcium Phosphate Deposition on Titanium Surfaces in the Presence of Fibronectin." *Journal of Biomedical Materials Research*. vol. 49, pp. 345-352.

Yamada, Norihiro and Katsuhiko Ariga. 2000. "Formation of β-Sheet Assemblage with a View to Developing an Amyloid Model." *Synlett*. vol. 5, pp. 575-586.

Yang, Lin and Paschalis Alexandridis. 2000. "Physicochemical Aspects of Drug Delivery and Release from Polymer-Based Colloids." *Current Opinion in Colloid & Interface Science*. vol. 5, pp. 132-143.

Yu, Huanran, Hiroshi Narusawa, Kisae Itoh, Akihiro Oshi, Narutoshi Yoshino, Kazuo Ohbu, Toshiaki Shirakawa, Kazuhiro Fukada, Masatoshi Fujii, Tadashi Kato, and Tsutomu Seimiya. 2000. "Hydrophilicity of Polar and Apolar Domains of Amphiphiles." *Journal of Colloid and Interface Science*. vol. 229, pp. 375-390.

Zhu, G., M. F. Mehler, P. C. Mabie, and J. A. Kessler. 2000. "Developmental Changes in Neural Progenitor Cell Lineage Commitment Do Not Depend on Epidermal Growth Factor Receptor Signaling." *Journal of Neuroscience Research*. vol. 59, pp. 312-320.

Orlic, Donald, Jan Kajstura, Stefano Chimenti, Igor Jakonuk, Stacie M. Anderson, Baosheng Li, James Pickel, Ronald McKay, Bernardo Nadal-Ginard, David M. Bodine, Annarosa Leri, and Piero Anversa. Apr. 5, 2001. "Bone Marrow Cells Regenerate Infarcted Myocardium." *Nature*. vol. 410, pp. 701-705.

Vailhé, Bruno, Daniel Vittet, and Jean-Jacques Feige. Apr. 2001. "In Vitro Models of Vasculogenesis and Angiogenesis." *Laboratory Investigation*. vol. 81, No. 4, pp. 439-452.

Davis, N. G., J. Teisen, C. Schuh, and D. C. Dunand. May 2001. "Solid-State Foaming of Titanium by Superplastic Expansion of Argon-Filled Pores." *J. Mater. Res*. vol. 16, No. 5, pp. 1508-1519.

Rabchevsky, Alexander G. and George M. Smith. May 2001. "Therapeutic Interventions Following Mammalian Spinal Cord Injury." *Arch. Neurol*. vol. 58, pp. 721-726.

Huang, Michael H., Samuel Mao, Henning Feick, Haoquan Yan, Yiying Wu, Hannes Kind, Eicke Weber, Richard Russo, and Peidong Yang. Jun. 8, 2001. "Room-Temperature Ultraviolet Nanowire Nanolasers." *Science*. vol. 292, pp. 1897-1899.

Lee, Kuen Yong and David J. Mooney. Jul. 2001. "Hydrogels for Tissue Engineering." *Chemical Reviews*. vol. 101, No. 7, pp. 1869-1879.

Aggeli, A., I. A. Nyrkova, M. Bell, R. Harding, L. Carrick, T. C. B. McLeish, A. N. Semenov, and N. Boden. Oct. 9, 2001. "Hierarchical Self-Assembly of Chiral Rod-Like Molecules as a Model for Peptide β-Sheet Tapes, Ribbons, Fibrils, and Fibers." *Proceedings of the National Academy of Sciences of the United States of America*. vol. 98, No. 21, pp. 11857-11862.

Richardson, Thomas P., Martin C. Peters, Alessandra B. Ennett, and David J. Mooney. Nov. 2001. "Polymeric System for Dual Growth Factor Delivery." *Nature Biotechnology*. vol. 19, pp. 1029-1034.

Mathew, Mathai and Shozo Takagi. Nov.-Dec. 2001. "Structures of Biological Minerals in Dental Research." *Journal of Research of the National Institute of Standards and Technology*. vol. 106, No. 6, pp. 1035-1044.

Woo, Byung Ho, Betsy F. Fink, Richard Page, Jay A. Schrier, Yeong Woo Jo, Ge Jiang, Michelle DeLuca, Henry C. Vasconez, and Patrick P. DeLuca. Dec. 2001. "Enhancement of Bone Growth by Sustained Delivery of Recombinant Human Bone Morphogenetic Protein-2 in a Polymeric Matrix." *Pharmaceutical Research*. vol. 18, No. 12, pp. 1747-1753.

Barrère, F., P. Layrolle, C. A. Van Blitterswijk, and K. de Groot. 2001. "Biomimetic Coatings on Titanium: A Crystal Growth Study of Octacalcium Phosphate." *Journal of Materials Science: Materials in Medicine*. vol. 12, pp. 529-534.

Bianco-Peled, Havazelet, Yoav Dori, James Schneider, Li-Piin Sung, Sushil Satija, and Matthew Tirrell. 2001. "Structural Study of Langmuir Monolayers Containing Lipidated Poly(ethylene glycol) and Peptides." *Langmuir*. vol. 17, No. 22, pp. 6931-6937.

Cavalli, M., G. Gnappi, A. Montenero, D. Bersani, P. P. Lottici, S. Kaciulis, G. Mattogno, and M. Fini. 2001. "Hydroxy- and Fluorapatite Films on Ti Alloy Substrates: Sol-gel Preparation and Characterization." *Journal of Materials Science*. vol. 36, pp. 3253-3260.

Chang, John C., Gregory J. Brewer, and Bruce C. Wheeler. 2001. "Modulation of Neural Network Activity by Patterning." *Biosensors & Bioelectronics*. vol. 16, pp. 527-533.

Chang, Sophia C. N., Jon A. Rowley, Geoffrey Tobias, Nicholas G. Genes, Amit K. Roy, David J. Mooney, Charles A. Vacanti, and Lawrence J. Bonassar. 2001. "Injection Molding of Chondrocyte/Alginate Constructs in the Shape of Facial Implants." *Journal of Biomedical Materials Research*. vol. 55, pp. 503-511.

Doi, Tomokiyo, Takatoshi Kinoshita, Hiroki Kamiya, Shintaro Washizu, Yoshiharu Tsujita, and Hiraoki Yoshimizu. 2001. "Aggregation of Polypeptide-Based Amphiphiles in Water." *Polymer Journal*. vol. 33, No. 2, pp. 160-164.

Gore, Tushar, Yoav Dori, Yeshayahu Talmon, Matthew Tirrell, and Havazelet Bianco-Peled. 2002. "Self-Assembly of Model Collagen Peptide Amphiphiles." *Langmuir*. vol. 17, No. 17, pp. 5352-5360.

Hoess, Ronald H. 2001. "Protein Design and Phage Display." *Chemical Reviews*. vol. 101, No. 10, pp. 3205-3218.

Huang, Eric J. and Louis F. Reichardt. 2001. "Neurotrophins: Roles in Neuronal Development and Function." *Annual Review of Neuroscience*. vol. 24, pp. 677-736.

Kam, L., W. Shain, J. N. Turner, and R. Bizios. 2001. "Axonal Outgrowth of Hippocampal Neurons on Micro-Scale Networks of Polylysine-Conjugated Laminin." *Biomaterials*. vol. 22, pp. 1049-1054.

Kikuchi, Masanori, Soichiro Itoh, Shizuko Ichinose, Kenichi Shinomiya, and Junzo Tanaka. 2001. "Self-Organization Mechanism in a Bone-Like Hydroxyapatite/Collagen Nancomposite Synthesized in Vitro and Its Biological Reaction in Vivo." *Biomaterials*. vol. 22, pp. 1705-1711.

Liu, Yuelian, Pierre Layrolle, Joost de Bruijn, Clemens van Blitterswijk, and Klaas de Groot. 2001. "Biomimetic Coprecipitation of Calcium Phosphate and Bovine Serum Albumin on Titanium Alloy." *Journal of Biomedical Materials Research*. vol. 57, pp. 327-335.

Look, D. C. 2001. "Recent Advances in ZnO Materials and Devices." *Materials Science and Engineering*. vol. B80, pp. 383-387.

Matsui, Hiroshi, and Gary E. Douberly, Jr. 2001. "Organization of Peptide Nanotubes into Macroscopic Bundles." *Langmuir*. vol. 17, No. 25, pp. 7918-7922.

Neet, K. E. and R. B. Campenot. 2001. "Receptor Binding, Internalization, and Retrograde Transport of Neurotrophic Factors." *CMLS, Cell Mol. Life Sci*. vol. 58, pp. 1021-1035.

Otsuka, Hidenori, Yukio Nagasaki, and Kazunori Kataoka. 2001. "Self-Assembly of Poly(ethylene glycol) -based Block Copolymers for Biomedical Applications." *Current Opinion in Colloid & Interface Science*. vol. 6, pp. 3-10.

Shimizu, Toshimi, Rika Iwaura, Mitsutoshi Masuda, Takeshi Hanada, and Kiyoshi Yase. 2001. "Internucleobase-Interaction-Directed Self-Assembly of Nanofibers from Homo- and Heteroditopic 1,ω-Nucleobase Bolaamphiphiles." *Journal of the American Chemical Society*. vol. 123, No. 25, pp. 5947-5955, S1-S16.

Socrates, George. 2001. *Infrared and Raman Characteristic Group Frequencies: Tables and Charts*. Third Edition. Chichester, England: John Wiley & Sons Ltd.

Spanos, Nikos and Petros G. Koutsoukos. 2001. "Model Studies of the Effect of Orthophospho-L-Serine on Biological Mineralization." *Langmuir*. vol. 17, No. 3, pp. 866-872.

Takadama, Hiroaki, Hyun-Min Kim, Tadashi Kokubo, and Takashi Nakamura. 2001. "TEM-EDX Study of Mechanism of Bonelike Apatite Formation on Bioactive Titanium Metal in Simulated Body Fluid." *Journal of Biomedical Materials Research*. vol. 57, pp. 441-448.

Tanihara, Masao, Yasuo Suzuki, Eriko Yamamoto, Atsushi Noguchi, and Yutaka Mizushima. 2001. "Sustained Release of Basic Fibroblast Growth Factor and Angiogenesis in a Novel Covalently Crosslinked Gel of Heparin and Alginate." *Journal of Biomedical Materials Research*. vol. 56, pp. 216-221.

Torchilin, Vladimir P. 2001. "Structure and Design of Polymeric Surfactant-Based Drug Delivery Systems." *Journal of Controlled Release*. vol. 73, pp. 137-172.

Yeung, C. K., L. Lauer, A. Offenhäusser, and W. Knoll. 2001. "Modulation of the Growth and Guidance of Rat Brain Stem Neurons Using Patterned Extracellular Matrix Proteins." *Neuroscience Letters*. vol. 301, pp. 147-150.

Zubarev, Eugene R., Martin U. Pralle, Eli D. Sone, and Samuel I. Stupp. 2001. "Self-Assembly of Dendron Rodcoil Molecules into Nanoribbons." *Journal of the American Chemical Society*. vol. 123, No. 17, pp. 4105-4106.

Hirschi, Karen K., Lihua Lai, Narasimhaswamy S. Belaguli, David A. Dean, Robert J. Schwartz, and Warren E. Zimmer. Feb. 22, 2002. "Transforming Growth Factor-β Induction of Smooth Muscle Cell Phenotype Requires Transcriptional and Post-transcriptional Control of Serum Response Factor." *The Journal of Biological Chemistry*. vol. 277, No. 8, pp. 6287-6295.

Xu, Weiming, Lizhi Liu, and Ian G. Charles. Feb. 2002. "Microencapsulated iNOS-expressing Cells Cause Tumor Suppression in Mice." *The FASEB Journal*. vol. 16, pp. 213-215.

Zubarev, Eugene R., Martin U. Pralle, Eli D. Stone, and Samuel I. Stupp. Feb. 2002. "Scaffolding of Polymers by Supremolecular Nanoribbons." *Advanced Materials*. vol. 14, No. 3, pp. 198-203.

Teng, Yang D., Erin B. Lavik, Xianlu Qu, Kook I. Park, Jitka Ourednik, David Zurakowski, Robert Langer, and Evan Y. Snyder. Mar. 5, 2002. "Functional Recovery Following Traumatic Spinal Cord Injury Mediated by a Unique Polymer Scaffold Seeded with Neural Stem Cells." *Proceedings of the National Academy of Sciences of the United States of America*. vol. 99, No. 5, pp. 3024-3029.

Bradbury, Elizabeth J., Lawrence D. F. Moon, Reena J. Popat, Von R. King, Gavin S. Bennett, Preena N. Patel, James W. Fawcett, and Stephen B. McMahon. Apr. 11, 2002. "Chondroitinase ABC Promotes Functional Recovery After Spinal Cord Injury." *Nature*. vol. 416, pp. 636-640.

Vauthey, Sylvain, Steve Santoso, Haiyan Gong, Nicki Watson, and Shuguang Zhang. Apr. 16, 2002. "Molecular Self-Assembly of Surfactant-like Peptides to Form Nanotubes and Nanovesicles." *Proceedings of the National Academy of Sciences of the United States of America*. vol. 99, No. 8, pp. 5355-5360.

Nowak, Andrew P., Victor Breedveld, Lisa Pakstis, Bulent Ozbas, David J. Pine, Darrin Pochan, and Timothy J. Deming. May 23, 2002. "Rapidly Recovering Hydrogel Scaffolds from Self-Assembling Diblock Copolypeptide Amphiphiles." *Nature*. vol. 417, pp. 424-428.

GrandPré, Tadzia, Shuxin Li, and Stephen M. Strittmatter. May 30, 2002. "Nogo-66 Receptor Antagonist Peptidek Promotes Axonal Regeneration." *Nature*. vol. 417, pp. 547-551.

Storch, Alexander and Johannes Schwarz. May 2002. "Neural Stem Cells and Neurodegeneration." *Current Opinion in Investigational Drugs*. vol. 3, No. 5, pp. 774-781.

Lendlein, Andreas and Robert Langer. May 31, 2002. "Biodegradable, Elastic Shape-Memory Polymers for Potential Biomedical Applications." *Science*. vol. 296, pp. 1673-1676.

Qiu, Jin, Dongming Cai, Haining Dai, Marietta McAttee, Paul N. Hoffman, Barbara S. Bregman, and Marie T. Filbin. Jun. 13, 2002. "Spinal Axon Regeneration Induced by Elevation of Cyclic AMP." *Neuron*. vol. 34, pp. 895-903.

Catledge, Shane A., Marc D. Fries, Yogesh K. Vohra, William R. Lacefield, Jack E. Lemons, Shanna Woodard, and Ramakrishna Venugopalan. Jun.-Aug. 2002. "Nanostructured Ceramics for Biomedical Implants." *Journal of Nanoscience and Nanotechnology*. vol. 2, No. 3/4, pp. 293-312.

Alsberg, Eben, Kenneth W. Anderson, Amru Albeiruti, Jon A. Rowley, and David J. Mooney. Sep. 17, 2002. "Engineering Growing Tissues." *Proceedings of the National Academy of Sciences of the United States of America*. vol. 99, No. 19, pp. 12025-12030.

Kay, Sarina, Anil Thapa, Karen M. Haberstroh, and Thomas J. Webster. Oct. 2002. "Nanostructured Polymer/Nanophase Ceramic Composites Enhance Osteoblast and Chondrocyte Adhesion." *Tissue Engineering*. vol. 8, No. 5, pp. 753-761.

Chang, Hua, Chester W. Brown, and Martin M. Matzuk. Dec. 2002. "Genetic Analysis of the Mammalian Transforming Growth Factor-β Superfamily." *Endocrine Reviews*. vol. 23, No. 6, pp. 787-823.

Canaple, Laurence, Annemie Rehor, and David Hunkeler. 2002. "Improving Cell Encapsulation Through Size Control." *J. Biomater. Sci. Polymer Edn.* vol. 13, No. 7, pp. 783-796.

Caplan, Michael R., Elissa M. Schwartzfarb, Shuguang Zhang, Roger D. Kamm, and Douglas A. Lauffenburger. 2002. "Control of Self-Assembling Oligopeptide Matrix Formation Through Systematic Variation of Amino Acid Sequence." *Biomaterials*. vol. 23, pp. 219-227.

Chen, Zhi Jiang, Yvonne Ughrin, and Joel M. Levine. 2002. "Inhibition of Axon Growth by Oligodendrocyte Precursor Cells." *Molecular and Cellular Neuroscience*. vol. 20, pp. 125-139.

Cornish, Toby, Darren W. Branch, Bruce C. Wheeler, and Jame T. Campanelli. 2002. "Microcontact Printing. A Versatile Technique for the Study of Synaptogenic Molecules." *Molecular and Cellular Neuroscience*. vol. 20, pp. 140-153.

Costa, Silvia, Thierry Planchenault, Cecile Charriere-Bertrand, Yann Mouchel, Christiane Fages, Sharon Juliano, Thierry Lefrançois, Georgia Barlovatz-Meimon, and Marcienne Tardy. 2002. "Astroglial Permissivity for Neuritic Outgrowth in Neuron-Astrocyte Cocultures Depends on Regulation of Laminin Bioavailability." *GLIA*. vol. 37, pp. 105-113.

Gariépy, Jean, Sandrine Rémy, Xiuguo Zhang, James R. Ballinger, Eleonora Bolewska-Pedyczak, Michael Rauth, and Stuart K. Bisland. 2002. "A Simple Two-Step Approach for Introducing a Protected Diaminedithiol Chelator During Solid-Phase Assembly of Peptides." *Bioconjugate Chem*. vol. 13, No. 3, pp. 679-684.

Glättli, Alice, Xavier Daura, Dieter Seebach, and Wilfred F. van Gunsteren. 2002. "Can One Derive the Confrontational Preference of a β-Peptide from Its CD Spectrum?" *Journal of the American Chemical Society*. vol. 124, No. 44, pp. 12972-12978.

Gutwein, Luke G. and Thomas J. Webster. 2002. "Osteoblast and Chrondrocyte Proliferation in the Presence of Alumina and Titania Nanoparticles." *Journal of Nanoparticle Research*. vol. 4, pp. 231-238.

Huang, Ning-Ping, Gabor Csucs, Kazunori Emoto, Yukio Nagasaki, Kazunori Kataoka, Marcus Textor, and Nicholas D. Spencer. 2002. "Covalent Attachment of Novel Poly(ethylene glycol)—Poly(DL-lactic acid) Copolymeric Micelles to $TiO_2$ Surfaces." *Langmuir*. vol. 18, No. 1, pp. 252-258.

Joshi, Mital and Michael G. Fehlings. 2002. "Development and Characterization of a Novel, Graded Model of Clip Compressive Spinal Cord Injury in the Mouse: Part 1. Clip Design, Behavioral Outcomes, and Histopathology." *Journal of Neurotrauma*. vol. 19, No. 2, pp. 175-190.

Joshi, Mital and Michael G. Fehlings. 2002. "Development and Characterization of a Novel, Graded Model of Clip Compressive Spinal Cord Injury in the Mouse: Part 2. Quantitative Neuroanatomical Assessment and Analysis of the Relationships Between Axonal Tracts, Residual Tissue, and Locomotor Recovery." *Journal of Neurotrauma*. vol. 19, No. 2, pp. 191-203.

Kruger, Ryan G., Patrick Dostal, and Dewey G. McCafferty. 2002. "An Economical and Preparative Orthogonal Solid Phase Synthesis of Fluorescein and Rhodamine Derivatized Peptides: FRET Substrates for the *Staphylococcus aureus* Sortase SrtA Transpeptidase Reaction." *Chem. Commun*. pp. 2092-2093.

Lauer, L., A. Vogt, C. K. Yeung, W. Knoll, and A. Offenhäusser. 2002. "Electrophysiological Recordings of Patterned Rat Brain Stem Slice Neurons." *Biomaterials*. vol. 23, pp. 3123-3130.

Lavik, Erin, Yang D. Teng, Evan Snyder, and Robert Langer. 2002. "Speeding Neural Stem Cells on Scaffolds of PGA, PLA, and Their Copolymers." *Methods in Molecular Biology: Neural Stem Cells: Methods and Protocols*. vol. 198, pp. 89-97.

Marini, Davide M., Wonmuk Hwang, Douglas A. Lauffenburger, Shuguang Zhang, and Roger D. Kamm. 2002. "Left-Handed Helical Ribbon Intermediates in the Self-Assembly of a β-Sheet Peptide." *Nano Letters*. vol. 2, No. 4, pp. 295-299.

Ohsaki, Mio, Tatsuya Okuda, Akihiro Wada, Toshiya Hirayama, Takuro Niidome, and Haruhiko Aoyagi. 2002. "In Vitro Gene Transfection Using Dendritic Poly(L-lysine)." *Bioconjugate Chem*. vol. 13, No. 3, pp. 510-517.

Okano, Hideyuki. 2002. "Stem Cell Biology of the Central Nervous System." *Journal of Neuroscience Research*. vol. 69, pp. 698-707.

Parmar, Malin, Charlotta Skogh, Anders Björklund, and Kenneth Campbell. 2002. "Regional Specification of Neurosphere Cultures Derived from Subregions of the Embryonic Telencephalon." *Molecular and Cellular Neuroscience*. vol. 21, pp. 645-656.

Porter, A. E., L. W. Hobbs, V. Benezra Rosen, and M. Spector. 2002. "The Ultrastructure of the Plasma-Sprayed Hydroxyapatite-bone Interface Predisposing to Bone Bonding." *Biomaterials*. vol. 23, pp. 725-733.

Rowley, Jon A. and David J. Mooney. 2002. "Alginate Type and RGD Density Control Myoblast Phenotype." *Journal of Biomedical Materials Research*. vol. 60, pp. 217-223.

Thiébaud, Pierre, Lara Lauer, Wolfgang Knoll, and Andreas Offenhäuser. 2002. "PDMS Device for Patterned Application of Microfluids to Neuronal Cells Arranged by Microcontact Printing." *Biosensors & Bioelectronics*. vol. 17, pp. 87-93.

Tryoen-Tóth, Petra, Dominique Vautier, Youssef Haikel, Jean-Claude Voegel, Pierre Schaaf, Johanna Chluba, and Joëlle Ogier. 2002. "Viability, Adhesion, and Bone Phenotype of Osteoblast-like Cells on Polyelectrolyte Multilayer Films." *Journal of Biomedical Materials Research*. vol. 60, pp. 657-667.

Young, Wise. 2002. "Spinal Cord Contusion Models." *Progress in Brain Research*. vol. 137, pp. 231-255.

Lutolf, Matthias P., Franz E. Weber, Hugo G. Schmoekel, Jason C. Schense, Thomas Kohler, Ralph Müller, and Jeffrey A. Hubbell. May 2003. "Repair of Bone Defects Using Synthetic Mimetics of Collagenous Extracellular Matrices." *Nature Biotechnology*. vol. 21, pp. 513-518.

Shaw, Derek and Molly S. Shoichet. May 2003. "Toward Spinal Cord Injury Repair Strategies: Peptide Surface Modification of Expanded Poly(Tetrafluoroethylene) Fibers for Guided Neurite Outgrowth in Vitro." *The Journal of Craniofacial Surgery*. vol. 14, No. 3, pp. 308-316.

Cheng, Hongwei, Wei Jiang, Frank M. Phillips, Rex C. Haydon, Ying Peng, Lan Zhou, Hue H. Luu, Naili An, Benjamin Breyer, Pantila Vanichakarn, Jan Paul Szatkowski, Jae Yoon Park, and Tong-Chuan He. Aug. 2003. "Osteogenic Activity of the Fourteen Types of Human Bone Morphogenetic Proteins (BMPs)." *The Journal of Bone & Joint Surgery*. vol. 85-A, No. 8, pp. 1544-1552, 141.

Pavlov, Georges, Stéphanie Finet, Karine Tatarenko, Evgueniya Komeeva, and Christine Ebel. 2003. "Conformation of Heparin Studied with Macromolecular Hydrodynamic Methods and X-ray Scattering." *Eur. Biophys. J.* vol. 32, pp. 437-449.

Arinzeh, Treena Livingston, Susan J. Peter, Michael P. Archambault, Christian van den Bos, Steve Gordon, Karl Kraus, Alan Smith, and Sudha Kadiyala. Oct. 2003. "Allogeneic Mesenchymal Stem Cells Regenerate Bone is a Critical-Sized Canine Segmental Defect." *The Journal of Bone & Joint Surgery*. vol. 85-A, No. 10, pp. 1927-1935.

Aggeli, Amalia, Mark Bell, Lisa M. Carrick, Colin W. G. Fishwick, Richard Harding, Peter J. Mawer, Sheena E. Radford, Andrew E. Strong, and Neville Boden. 2003. "pH as a Trigger of Peptide β-Sheet Self-Assembly and Reversible Switching Between Nematic and Isotropic Phases." *Journal of the American Chemical Society*. vol. 125, No. 32, pp. 9619-9628.

Alsina, Jordi and Fernando Albericio. 2003. "Solid-Phase Synthesis of C-Terminal Modified Peptides." *Biopolymers (Peptide Science)*. vol. 71, pp. 454-477.

Anthony, Shawn G. 2003. "Injectable Biomaterials for Bone Tissue Engineering."

Boontheekul, Tanyarut and David J. Mooney. 2003. "Protein-Based Signaling Systems in Tissue Engineering." *Current Opinion in Biotechnology*. vol. 14, pp. 559-565.

Fauza, Dario O. 2003. "Tissue Engineering: Current State of Clinical Application." *Current Opinion in Pediatrics*. vol. 15, pp. 267-271.

Ganesh, S. and R. Jayakurnar. 2003. "Structural Transitions Involved in a Novel Amyloid-Like β-Sheet Assemblage of Tripeptide Derivatives." *Biopolymers*. vol. 70, pp. 336-345.

Ganesh, S., S. Prakash, and R. Jayakumar. 2003. "Spectroscopic Investigation on Gel-Forming β-Sheet Assemblage of Peptide Derivatives." *Biopolymers*. vol. 70, pp. 346-354.

Gergely, C. S., P. Bar Yosef, R. Govrin-Lippman, F. Cuisinier, and H. Füredi-Milhofer. 2003. "The Deposition of Calcium Phosphates Within Polyelectrolyte Multilayer Films." *Key Engineering Materials*. vols. 240-242 (Bioceramics), pp. 287-290.

Goeden-Wood, Nichole L., Jay D. Keasling, and Susan J. Muller. 2003. "Self-Assembly of a Designed Protein Polymer into β-Sheet Fibrils and Responsive Gels." *Macromolecules*. vol. 36, No. 8, pp. 2932-2938.

Ishihara, Masayuki, Kiyohaya Obara, Toshiaki Ishizuka, Masanori Fujita, Masato Sato, Kazunori Masuoka, Yoshio Saito, Hirofumi Yura, Takemi Matsui, Hidemi Hattori, Makoto Kikuchi, and Akira Kurita. 2003. "Controlled Release of Fibroblast Growth Factors and Heparin from Photocrosslinked Chitosan Hydrogels and Subsequent Effect on in Vivo Vascularization." *Journal of Biomedical Materials Research*. vol. 64A, pp. 551-559.

Malkar, Navdeep B., Janelle L. Lauer-Fields, Darius Juska, and Gregg B. Fields. 2003. "Characterization of Peptide-Amphiphiles Possessing Cellular Activation Sequences." *Biomacromolecules*. vol. 4, No. 3, pp. 518-528.

Steward, Oswald, Binhai Zheng, and Marc Tessier-Lavigne. 2003. "False Resurrections: Distinguishing Regenerated from Spared Axons in the Injured Central Nervous System." *The Journal of Comparative Neurology*. vol. 459, pp. 1-8.

Wu, Sufan, Yoshihisa Suzuki, Yoko Ejiri, Toru Noda, Hongliang Bai, Masaaki Kitada, Kazuya Kataoka, Masayoshi Ohta, Hirotomi Chou, and Chizuka Ide. 2003. "Bone Marrow Stromal Cells Enhance Differentiation of Cocultured Neurosphere Cells and Promote Regeneration of Injured Spinal Cord." *Journal of Neuroscience Research*. vol. 72, pp. 343-351.

Yamada, Norihiro, Tsukasa Komatsu, Hirotsugu Yoshinaga, Kayo Yoshizawa, Susumu Edo, and Masashi Kunitake. 2003. "Self-Supporting Elastic Film without Covalent Linkages as a Hierarchically Integrated β-Sheet Assembly." *Angew. Chem. Int. Ed*. vol. 42, pp. 5496-5499.

Zhang, Yan, Hongwei Gu, Zhimou Yang, and Bing Xu. 2003. "Supramolecular Hydrogels Respond to Ligand-Receptor Interaction." *Journal of the American Chemical Society*. vol. 125, No. 45, pp. 13680-13681.

Hirano, Yoshiaki and David J. Mooney. Jan. 5, 2004. "Peptide and Protein Presenting Materials for Tissue Engineering." *Advanced Materials*. vol. 16, No. 1, pp. 17-25.

Silva, Gabriel A., Catherine Czeisler, Krista L. Niece, Elia Beniash, Daniel A. Harrington, John A. Kessler, and Samuel I. Stupp. Feb. 27, 2004. "Selective Differentiation of Neural Progenitor Cells by High-Epitope Density Nanofibers." *Science*. vol. 303, pp. 1352-1355.

Faulkner, Jill R., Julia E. Herrmann, Michael J. Woo, Keith E. Tansey, Ngan B. Doan, and Michael V. Sofroniew. Mar. 3, 2004. "Reactive Astrocytes Protect Tissue and Preserve Function after Spinal Cord Injury." *The Journal of Neuroscience*. vol. 24, No. 9, pp. 2143-2155.

Cao, Renhai, Anna Eriksson, Hajime Kubo, Kari Alitalo, Yihai Cao, Johan Thyberg. Mar. 19, 2004. "Comparative Evaluation of FGF-2-, VEGF-A-, and VEGF-C-Induced Angiogenesis, Lymphangiogenesis, Vascular Fenestrations, and Permeability." *Circulation Research*. vol. 94, pp. 664-670.

Anthony, Shawn G. Mar. 28-Apr. 1, 2004. "Self-Assembling Nanofiber Matrix for Bone Regeneration." *The 227th ACS National Meeting*. Anaheim, CA.

Donners, Jack J. M. Mar. 28-Apr. 1, 2004. "Growth Factor Binding Self-Assembling Nanofiber Networks for Tissue Regeneration." *The 227th ACS National Meeting*. Anaheim, CA.

Nikulina Elena, J. Lille Tidwell, Hai Ning Dai, Barbara S. Bregman, and Marie T. Filbin. Jun. 8, 2004. "The Phosphodiesterase Inhibitor Rolipram Delivered after a Spinal Cord Lesion Promotes Axonal Regeneration and Functional Recovery." *Proceedings of the National Academy of Sciences of the United States of American*. vol. 101, No. 23, pp. 8786-8790.

Pearse, Damien D., Francisco C. Pereira, Alexander E. Marcillo, Margaret L. Bates, Yerko A. Berrocal, Marie T. Filbin, and Mary Bartlett Bunge. Jun. 2004. "cAMP and Schwann Cells Promote Axonal Growth and Functional Recovery After Spinal Cord Injury." *Nature Medicine*. vol. 10, No. 6, pp. 610-616.

Lu, Paul, Hong Yang, Leonard L. Jones, Marie T. Filbin, and Mark H. Tuszynski. Jul. 14, 2004. "Combinatorial Therapy with Neurotrophins and cAMP Promotes Axonal Regeneration beyond Sites of Spinal Cord Injury." *The Journal of Neuroscience*. vol. 24, No. 28, pp. 6402-6409.

Lee, K. W., J. J. Yoon, J. H. Lee, S. Y. Kim, H. J. Jung, S. J. Kim, J. W. Joh, H. H. Lee, D. S. Lee, and S. K. Lee. 2004. "Sustained Release of Vascular Endothelial Growth Factor From Calcium-Induced Alginate Hydrogels Reinforced by Heparin and Chitosan." *Transplantation Proceedings*. vol. 36, pp. 2464-2465.

Matsumura, Sachiko, Shinobu Uemura, and Hisakazu Mihara. 2004. "Fabrication of Nanofibers with Uniform Morphology by Self-Assembly of Designed Peptides." *Chem. Eur. J*. vol. 10, pp. 2789-2794.

Sieminski, A. L., R. P. Hebbel, and K. J. Gooch. 2004. "The Relative Magnitudes of Endothelial Force Generation and Matrix Stiffness Modulate Capillary Morphogenesis in Vitro." *Experimental Cell Research*. vol. 297, pp. 574-584.

Vandermeulen, Guido W. M. and Harm-Anton Klok. 2004. "Peptide/Protein Hybrid Materials: Enhanced Control of Structure and Improved Performance through Conjugation of Biological and Synthetic Polymers." *Macromolecular Bioscience*. vol. 4, pp. 383-398.

Wang, Lin-Fa and Meng Yu. 2004. "Epitope Identification and Discovery Using Phage Display Libraries: Applications in Vaccine Development and Diagnostics." *Current Drug Targets*. vol. 5, No. 1, pp. 1-15.

Sayle, Roger. Printed Nov. 9, 2005. "Physiological Ionization and pKa Prediction." http://www.daylight.com/meetings/emug00/Sayle/pkapredict.html. pp. 1-13.

Bull, Steve R., Mustafa O. Guler, Rafael E. Bras, Thomas J. Meade, and Samuel I. Stupp. 2005. "Self-Assembled Peptide Amphiphile Nanofibers Conjugated to MRI Contrast Agents." *Nano Letters*. vol. 5, No. 1, pp. 1-4.

Guler, Mustafa O., Stephen Soukasene, James F. Hulvat, and Samuel I. Stupp. 2005. "Presentation and Recognition of Biotin on Nanofibers Formed by Branched Peptide Amphiphiles." *Nano Letters*. vol. 5, No. 1, pp. 249-252.

Loudon, M. "Amino Acid Structures at Physiological pH." Printed Jun. 5, 2006. www.brynmawr.edu/Acads/Chem/mnerzsto/amino_acids.htm, amino_acids_2.gif, and amino_acids3.htm.

Nomizu, Motoyoshi, Keizo Yamamura, Hynda K. Kleinman, and Yoshihiko Yamada. Aug. 1, 1993. "Multimeric Forms of Tyr-Ile-Gly-Ser-Arg (YIGSR) Peptide Enhance the Inhibition of Tumor Growth and Metastasis." Cancer Research. vol. 53, pp. 3459-3461.

Matsui, Hiroshi and Robert MacCuspie. Dec. 2001. "Metalloporphyrin Nanotube Fabrication Using Peptide Nanotubes as Templates." Nano Letters. vol. 1, No. 12, pp. 671-675.

Irvine, Darrell J. and Anne M. Mayes. 2001. "Nanoscale Clustering of RGD Peptides at Surfaces Using Comb Polymers. 1. Synthesis and Characterization of Comb Thin Films." Biomacromolecules. vol. 2, No. 1, pp. 85-94.

Matsui, Hiroshi, Precila Porrata, and Gary E. Douberly, Jr. 2001. "Protein Tubule Immobilization on Self-Assembled Monolayers on Au Substrates." Nano Letters. vol. 1, No. 9, pp. 461-464.

"AccessScience Search Results. Amphiphile." Accessed online May 7, 2007. http://www.accessscience.com/search/asearch?location=titlestext&newSearch=1&pubpriv=private&categories=dictionary&categval=dictionary&text=amphiphile.

McGraw-Hill Encyclopedia of Science & Technology Online.

Jackowski, Andre. 1995. "Neural Injury Repair: Hope for the Future as Barriers to Effective CNS Regeneration Become Clearer." J. Neurosurg. vol. 9, pp. 303-317.

Copping, Aaron M. and Vanda R. G. Pond. Dec. 9, 1950. "Folic Acid as a Growth-Factor for the Rat." Nature. No. 4232, p. 993.

Mulloy, Barbara and Mark J. Forster. 2000. "Conformation and Dynamics of Heparin and Heparan Sulfate." Glycobiology. vol. 10, No. 11, pp. 1147-1156.

Bruggeman, Holger, Sebastian Baumer, Wolfgang Florian Fricke, Arnim Wiezer, Heiko Liesegang, Iwona Decker, Christina Herzberg, Rosa Martinez-Arias, Rainer Merkl, Anke Henne, and Gerhard Gottschalk. Feb. 4, 2003. "The Genome Sequence of Clostridium tetani, the Causative Agent of Tetanus Disease." PNAS. vol. 100, No. 3, pp. 1316-1321.

Invitrogen. Printed Jan. 22, 2008. "Dulbecco's Modified Eagle Medium (D-MEM) (1X) Liquid (High Glucose)." http://www.invitrogen.com/content.cfm?pageId=95&fuseaction=MediaForm.dsp_mediaForm&productId....

Uniprot entry for Q899Z6. Printed Mar. 14, 2008. http://www.pir.uniprot.org/cgi-bin/upEntry?id=Q899Z6_CLOTE. 3 pages.

Tam, James P. 1996. "Recent Advances in Multiple Antigen Peptides." Journal of Immunological Methods. vol. 196, pp. 17-32.

Merkler, Doron, Gerlinde A. S. Metz, Olivier Raineteau, Volker Dietz, Martin E. Schwab, and Karim Fouad. May 15, 2001. "Locomotor Recovery in Spinal Cord-Injured Rats Treated with an Antibody Neutralizing the Myelin-Associated Neurite Growth Inhibitor Nogo-A." The Journal of Neuroscience. vol. 21, No. 10, pp. 3665-3673.

Bonnet, Dominique, Kacer Thiam, Estelle Loing, Oleg Melnyk, and Hèléne Gras-Masse, 2001. Synthesis by Chemoselective Ligation and Biological Evaluation of Novel Cell-Permeable PKC-τ Pseudosubstrate Lipopeptides. J. Med. Chem. vol. 44, No. 3, pp. 468-471.

Grothe, Claudia and Guido Nikkhah. 2001. "The role of Basic Fibroblast Growth Factor in Peripheral Nerve Regeneration." Anat. Embryol. vol. 204, pp. 171-177.

Silva, G. A., C. Czeisler, K. L. Niece, E. Beniash, J. D. Hartgerink, J. A. Kessler, and S. I. Stupp. Nov. 2-7, 2002. "Development of Neural Progenitor Cells Encapsulated in a Peptide Amphiphile Substrate That Is Induced to Self-Assemble Under Physiological Conditions." Biosis. Society for Neuroscience Abstract Viewer and Itinerary Planner—2002. Abstract No. 825.4. 32nd Annual Meeting of the Society for Neuroscience; Orlando, Florida.

Leng, J., S. U. Egelhaaf, and M. E. Cates. Sep. 2003. "Kinetics of the Micelle-to-Vesicle Transition: Aqueous Lecithin-Bile Salt Mixtures." Biophysical Journal. vol. 85, No. 3, pp. 1624-1646.

Kibbey, Maura C., Mathias Jucker, Benjamin S. Weeks, Rachael L. Neve, William E. Van Nostrand, and Hynda K. Kleinman. Nov. 1993. "β-Amyloid Precursor Protein Binds to the Neurite-Promoting IKVAV Site of Laminin." Proc. Natl. Acad. Sci. U.S.A. vol. 90, pp. 10150-10153.

Oka, Kazunari, Masaaki Yamamoto, Toshiharu Nonaka, and Masamichi Tomonaga. Apr. 1996. "The Significance of Artificial Cerebrospinal Fluid as Perfusate and Endoneurosurgey." Neurosurgery Online. vol. 38, No. 4, pp. 733-736.

Rapaport, Hanna, Kristian Kjaer, Torben R. Jensen, Leslie Leiserowitz, and David A. Tirrell. 2000. "Two-Dimensional Order in β-Sheet Peptide Monolayers." Journal of the American Chemical Society. vol. 122, No. 50, pp. 12523-12529.

Avrahami, Dorit and Yechiel Shai. 2002. "Conjugation of a Magainin Analogue with Lipophilic Acids Controls Hydrophobicity, Solution Assembly, and Cell Selectivity." Biochemistry. vol. 41, No. 7, pp. 2254-2263.

Yamada, Masanori, Yuichi Kadoya, Shingo Kasai, Kozue Kato, Mayumi Mochizuki, Norio Nishi, Nobuhisa Watanabe, Hynda K. Kleinman, Yoshihiko Yamada, and Motoyoshi Nomizu. 2002. "Ile-Lys-Val-Ala-Val (IKVAV)-Containing Laminin α1 Chain Peptides Form Amyloid-like Fibrils." FEBS Letters. vol. 530, pp. 48-52.

McGregor, Clare-Louise, Lu Chen, Neil C. Pomroy, Peter Hwang, Sandy Go, Avijit Chakrabartty, and Gilbert G. Privé. Feb. 2003. "Lipopeptide Detergents Designed for the Structural Study of Membrane Proteins." Nature Biotechnology. vol. 21, pp. 171-176.

Ohmori, Hideya, Yasumitsu Sato, and Akiyoshi Namiki. 2004. "The Anticonvulsant Action of Propofol on Epileptiform Activity in Rat Hippocampal Slices." Anesth. Analg. vol. 99, pp. 1095-1101.

Shahraki, Ali and Trevor W. Stone. 2004. "Blockade of Presynaptic Adenosine A1 Receptor Responses by Nitric Oxide and Superoxide in Rat Hippocampus." European Journal of Neuroscience. vol. 20, pp. 719-728.

Sone, Eli D. and Samuel I. Stupp. 2004. "Semiconductor-Encapsulated Peptide-Amphiphile Nanofibers." Journal of the American Chemical Society. vol. 126, No. 40, pp. 12756-12757.

Smith, L. A. and P. X. Ma. 2004. "Nano-Fibrous Scaffolds for Tissue Engineering." Colloids and Surfaces. B: Biointerfaces. vol. 39, pp. 125-131.

Tsonchev, Stefan, George C. Schatz, and Mark A. Ratner. 2004. "Electrostatically-Directed Self-Assembly of Cylindrical Peptide Amphiphile Nanostructures." J. Phys. Chem. B. vol. 108, No. 26, pp. 8817-8822.

Tsonchev, Stefan, Alessandro Troisi, George C. Schatz, and Mark A. Ratner. 2004. "All-Atom Numerical Studies of Self-Assembly of Zwitterionic Peptide Amphiphiles." J. Phys. Chem. B. vol. 108, No. 39, pp. 15278-15284.

Tsonchev, Stefan, Alessandro Troisi, George C. Schatz, and Mark A. Ratner. 2004. "On the Structure and Stability of Self-Assembled Zwitterionic Peptide Amphiphiles: A Theoretical Study." Nano Letters. vol. 4, No. 3, pp. 427-431.

Arnold, Michael S., Mustafa O. Guler, Mark C. Hersam, and Samuel I. Stupp. 2005. "Encapsulation of Carbon Nanotubes by Self-Assembling Peptide Amphiphiles." Langmuir. vol. 21, No. 10, pp. 4705-4709.

Behanna, Heather A., Jack J. J. M. Donners, Alex C. Gordon, and Samuel I. Stupp. 2005. "Coassembly of Amphiphiles with Opposite Peptide Polarities into Nanofibers." Journal of the American Chemical Society. vol. 127, No. 4, pp. 1193-1200.

Bitton, Ronit, Judith Schmidt, Markus Biesalski, Raymond Tu, Matthew Tirrell, and Havazelet Bianco-Peled. 2005. "Self-Assembly of Model DNA-Binding Peptide Amphiphiles." Langmuir. vol. 21, No. 25, pp. 11888-11895.

Bull, Steve R., Mustafa O. Guler, Rafael E. Bras, Palamadai N. Venkatasubramanian, Samuel I. Stupp, and Thomas J. Meade. 2005. "Magnetic Resonance Imaging of Self-Assembled Biomaterial Scaffolds." Bioconjugate Chem. vol. 16, No. 6, pp. 1343-1348.

de Loos, Maaike, Ben L. Feringa, and Jan H. van Esch. 2005. "Design and Application of Self-Assembled Low Molecular Weight Hydrogels." Eur. J. Org. Chem. pp. 3615-3631.

Guler, Mustafa O., Randal C. Claussen, and Samuel I. Stupp. 2005. "Encapsulation of Pyrene Within Self-Assembled Peptide Amphiphile Nanofibers." Journal of Materials Chemistry. vol. 15, pp. 4507-4512.

Guler, Mustafa O., Jonathan K. Pokorski, Daniel H. Appella, and Samuel I. Supp. 2005. "Enhanced Oligonucleotide Binding to Self-Assembled Nanofibers." Bioconjugate Chem. vol. 16, No. 3, pp. 501-503.

Jun, Ho-Wook, Virany Yuwono, Sergey E. Paramonov, and Jeffrey D. Hartgerink. 2005. "Enzyme-Mediated Degradation of Peptide-Amphiphile Nanofiber Networks." Adv. Mater. vol. 17, pp. 2612-2617.

Silva, Gabriel A. 2005. "Nanotechnology Approaches for the Regeneration and Neuroprotection of the Central Nervous System." Surgical Neurology. vol. 63, pp. 301-306.

Silva, Gabriel A. 2005. "Small Neuroscience: The Nanostructure of the Central Nervous System and Emerging Nanotechnology Applications." Current Nanoscience. vol. 1, No. 3, pp. 225-236.

Solis., F. J., S. I. Stupp, and M. Olvera de la Cruz. 2005. "Charge Induced Pattern Formation on Surfaces: Segregation in Cylindrical Micelles of Cationic-Anionic Peptide-Amphiphiles." The Journal of Chemical Physics. vol. 122, No. 5, 054905-1-054905-9.

Tovar, John D., Randal C. Claussen, and Samuel I. Stupp. 2005. "Probing the Interior of Peptide Amphiphile Supramolecular Aggregates." Journal of the American Chemical Society. vol. 127, No. 20, pp. 7337-7345.

Hosseinkhani, Hossein, Mohsen Hosseinkhani, and Hisatoshi Kobayashi. Jul. 2006. "Design of Tissue-Engineered Nanoscaffold Through Self-Assembly of Peptide Amphiphile." Journal of Bioactive and Compatible Polymers. vol. 21, No. 4, pp. 277-296.

Engler, Adam J., Shamik Sen, H. Lee Sweeney, and Dennis E. Discher. Aug. 25, 2006. "Matrix Elasticity Directs Stem Cell Lineage Specification." Cell. vol. 126, pp. 677-689.

Brunsveld, L., J. Kuhlmann, and H. Waldmann. 2006. "Synthesis of Palmitoylated Ras-Peptides and -Proteins." Methods. vol. 40, pp. 151-165.

Elgersma, Ronald C., Tania Meijneke, Remco de Jong, Arwin J. Brouwer, George Posthuma, Dirk T. S. Rijkers, and Rob M. J. Liskamp. 2006. "Synthesis and Structural Investigations of N-alkylated β-peptidosulfonamide-peptide Hybrids of the Amyloidogenic Amylin(20-29) Sequence: Implications of Supramolecular Folding for the Design of Peptide-Based Bionanomaterials." Organic & Biomolecular Chemistry. vol. 4, pp. 3587-3597.

Guler, Mustafa O., Lorraine Hsu, Stephen Soukasene, Daniel A. Harrington, James F. Hulvat, and Samuel I. Stupp. 2006. "Presentation of RGDS Epitopes on Self-Assembled Nanofibers of Branched Peptide Amphiphiles." Biomacromolecules. vol. 7, No. 6, pp. 1855-1863.

Harrington, Daniel A., Earl Y. Cheng, Mustafa O. Guler, Leslie K. Lee, Jena L. Donovan, Randal C. Claussen, and Samuel I. Stupp. 2006. "Branched Peptide-Amphiphiles as Self-Assembling Coatings for Tissue Engineering Scaffolds." Journal of Biomedical Materials Research Part A. pp. 157-167.

Hosseinkhani, Hossein, Mohsen Hosseinkhani, Ali Khademhosseini, Hisatoshi Kobayashi, and Yasuhiko Tabata. 2006. "Enhanced Angiogenesis Through Controlled Release of Basic Fibroblast Growth Factor from Peptide Amphiphile for Tissue Regeneration." Biomaterials. vol. 27, pp. 5836-5844.

Mardilovich, Anastasia, Jennifer A. Craig, Matthew Q. McCammon, Ashish Garg, and Efrosini Kokkoli. 2006. "Design of a Novel Fibronectin-Mimetic Peptide-Amphiphile for Functionalized Biomaterials." Langmuir. vol. 22, No. 7, pp. 3259-3264.

Paramonov, Sergey E., Ho-Wook Jun, and Jeffrey D. Hartgerink. 2006. "Self-Assembly of Peptide Amphiphile Nanofibers: The Roles of Hydrogen Bonding and Amphiphilic Packing." Journal of the American Chemical Society. vol. 128, No. 22, pp. 7291-7298.

Rajangam, Kanya, Heather A. Behanna, Michael J. Hui, Xiaoqiang Han, James F. Hulvat, Jon W. Lomasney, and Samuel I. Stupp. 2006. "Heparin Binding Nanostructures to Promote Growth of Blood Vessels." Nano Letters. vol. 6, No. 9, pp. 2086-2090.

Reches, Meital and Ehud Gazit. 2006. "Molecular Self-Assembly of Peptide Nanostructures: Mechanism of Association and Potential Uses." Current Nanoscience. vol. 2, No. 2, pp. 105-111.

Stendahl, John C., Mukti S. Rao, Mustafa O. Guler, and Samuel I. Stupp. 2006. "Intermolecular Forces in the Self-Assembly of Peptide Amphiphile Nanofibers." Advanced Functional Materials. vol. 16, pp. 499-508.

Behanna, Heather A., Kanya Rajangam, and Samuel I. Stupp. 2007. "Modulation of Fluorescence Through Coassembly of Molecules in Organic Nanostructures." Journal of the American Chemical Society. vol. 129, No. 2, pp. 321-327.

Meijer, Joris T., Marjolijn Roeters, Valentina Viola, Dennis W. P. M. Löwik, Gert Vriend, and Jan C. M. van Hest. 2007. "Stabilization of Peptide Fibrils by Hydrophobic Interaction." Langmuir. vol. 23, No. 4, pp. 2058-2063.

Nomizu, Motoyoshi, Atsushi Utani, Norio Shiraishi, Maura C. Kibbey, Yoshihiko Yamada, and Peter P. Roller. Jul. 15, 1992. "The All-D-Configuration Segment Containing the IKVAV Sequence of Laminin A Chain Has Similar Activities to the All-L-Peptide in Vitro and in Vivo." The Journal of Biological Chemistry. vol. 267, No. 20, pp. 14118-14121.

Margomenou-Leonidopoulou, G. 1994. "Thermotropic Mesophases of Ionic Amphiphiles. II. Ionic Amphiphiles in Aqueous Media." Journal of Thermal Analysis. vol. 42, pp. 1041-1061.

Rappolt, Michael and Gert Rapp. 1996. "Structure of the Stable and Metastable Ripple Phase of Dipalmitoylphosphatidylcholine." Eur. Biophys. J. vol. 24, pp. 381-386.

Goveas, J. L. and S. T. Milner. 1997. "Dynamics of the Lamellar—Cylindrical Transition in Weakly Segregated Diblock Copolymer Melts." Macromolecules. vol. 30, No. 9, pp. 2605-2612.

Munson, John B. and Stephen B. McMahon. 1997. "Effects of GDNF on Axotomized Sensory and Motor Neurons in Adult Rats." European Journal of Neuroscience. vol. 9, pp. 1126-1129.

Femandez, A., M. A. Alsina, I. Haro, R. Galantai, and F. Reig. 1998. "Synthesis and Physicochemical Characterization of Cyclic Laminin Related Peptides." Langmuir. vol. 14, No. 13, pp. 3625-3630.

Yagi, Nobuhiro, Yoshikatsu Ogawa, Masato Kodaka, Tomoko Okada, Takenori Tomohiro, Takeo Konakahara, and Hiroaki Okuno. 1999. "A Surface-Modified Functional Liposome Capable of Binding to Cell Membranes." Chem. Commun. pp. 1687-1688.

Luo, Yi and Glenn D. Prestwich. 2001. "Novel Biomaterials for Drug Delivery." Expert. Opin. Ther. Patents. vol. 11, No. 9, pp. 1395-1410.

Marchi-Artzner, Valerie, Barabara Lorz, Ulrike Hellerer, Martin Kantlehner, Horst Kessler, and Erich Sackmann. 2001. "Selective Adhesion of Endothelial Cells to Artificial Membranes with a Synthetic RGD-Lipopeptide." Chem. Eur. J. vol. 7, No. 5, pp. 1095-1101.

Blight, Andrew R. Nov. 2002. "Miracles and Molecules—Progress in Spinal Cord Repair." Nature Neuroscience Supplement. vol. 5, pp. 1051-1054.

Rodger, Alison, Jascindra Rajendra, Rachel Marrington, Malin Ardhammar, Bengt Norden, Jonathan D. Hirst, Andrew T. B. Gilbert, Timothy R. Dafforn, David J. Halsall, Cheryl A. Woolhead, Colin Robinson, Teresa J. T. Pinheiro, Jurate Kazlauskaite, Mark Seymour, Niuvis Perez, and Michael J. Hannon. 2002. "Flow Oreinted Linear Dichroism to Probe Protein Orientation in Membrane Environments." Phys. Chem. Chem. Phys. vol. 4, pp. 4051-4057.

Silva, G. A., K. L. Kehl, K. L. Niece, and S. I. Stupp. May 4, 2003. "Nanoengineered Peptide Amphiphile Network for Photoreceptor Replacement in Degenerative Retinal Disorders." Investigative Ophthalmology & Visual Science. Abstract No. 492 from Annual Meeting of the Association for Research in Vision and Opthalmology.

Brandenburg, Klaus, Frauke Wagner, Mareiki Muller, Holger Heine, Jorg Andra, Michel H. J. Koch, Ulrich Zahringer, and Ulrich Seydel. 2003. "Physicochemical Characterization and Biological Activity of a Glycoglycerolipid from Mycoplasma fermentans." Eur. J. Biochem. vol. 270, pp. 3271-3279.

Czeisler, C., V. M. Tysseling-Mattiace, G. A. Silva, S. I. Stupp, and J. A. Kessler. 2003. "Behavioral Improvement and Increased Survival Rate after Treatment with a Self Assembling Gel in a Rat Model of Spinal Cord Injury." 2003 Abstract Viewer/Itinerary Planner. Program No. 245.22. Washington, DC: Society for Neuroscience. Printed Feb. 5, 2007. p. 1. http://sfn.scholarone.com/itin2003/main.html?new_page_id=126&abstract_id=1554....

Schmidt, Christine E. and Jennie Baier Leach. 2003. "Neural Tissue Engineering: Strategies for Repair and Regeneration." Annu. Rev. Biomed. Eng. vol. 5, pp. 293-347.

t' Hart, Bert A. and Sandra Amor. 2003. "The Use of Animal Models to Investigate the Pathogenesis of Neuroinflammatory Disorders of the Central Nervous System." Current Opinion in Neurology. vol. 16, pp. 375-383.

Beniash, Elia, Jeffery D. Hartgerink, Hannah Storrie, John C. Stendahl, and Samuel I. Stupp. 2005. "Self-Assembling Peptide Amphiphile Nanofiber Matrices for Cell Entrapment." Acta Biomaterialia. vol. 1, pp. 387-397.

Hoke, Ahmet. Aug. 2006. "Mechanisms of Disease: What Factors Limit the Success of Peripheral Nerve Regeneration in Humans?" Nature Clinical Practice Neurology. vol. 2, No. 8, pp. 448-454.

Kokkoli, Efrosini, Anastasia Mardilovich, Alison Wedekind, Emilie L. Rexeisen, Ashish Garg, and Jennifer A. Craig. 2006. "Self-Assembly and Applications of Biomimetic and Bioactive Peptide-Amphiphiles." Soft Matter. vol. 2, pp. 1015-1024.

The LabRat.com. 2007. updated. Hank's Buffered Salt Solution (HBSS) Recipe. http://www.thelabrat.com/protocolsHanks.shtml. Printed Jan. 19, 2007. pp. 1-2.

* cited by examiner

Molecule 1

Molecule 2

SEQUENCE LISTING

<160> NUMBER OF SEQ ID NOS: 22

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ile Lys Val Ala Val
 1               5

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Ser(P)

<400> SEQUENCE: 2

Cys Cys Cys Cys Gly Gly Gly Ser Arg Gly Asp
 1               5                  10

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Cys Cys Cys Cys Gly Gly Gly Glu Ile Lys Val Ala Val
 1               5                  10

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Cys Cys Cys Arg Phe Glu Phe Arg Phe Glu Phe Arg
 1               5                  10

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Ser(A)

<400> SEQUENCE: 5

```
Cys Cys Cys Cys Gly Gly Gly Ser Arg Gly Asp
 1               5                  10
```

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

```
Tyr Ile Gly Ser Arg
 1               5
```

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Ser(P)

<400> SEQUENCE: 7

```
Cys Cys Cys Cys Gly Gly Gly Ser
 1               5
```

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Ser(P)

<400> SEQUENCE: 8

```
Gly Gly Gly Ser Arg Gly Asp
 1               5
```

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Ser(P)

<400> SEQUENCE: 9

```
Ala Ala Ala Ala Gly Gly Gly Ser Arg Gly Asp
 1               5                  10
```

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (8)
<223> OTHER INFORMATION: Ser(P)

<400> SEQUENCE: 10

Cys Cys Cys Cys Gly Gly Gly Ser Lys Gly Glu
 1               5                  10

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Ser(P)

<400> SEQUENCE: 11

Ala Ala Ala Ala Gly Gly Gly Ser Lys Gly Glu
 1               5                  10

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Cys Cys Cys Cys Gly Gly Gly Ser Arg Gly Asp
 1               5                  10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Ser(P)

<400> SEQUENCE: 13

Cys Cys Cys Cys Gly Gly Gly Ser Arg Gly Asp Ser
 1               5                  10

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: Ser(P)
<220> FEATURE:
<221> NAME/KEY: MOD_RES
<222> LOCATION: (11)
<223> OTHER INFORMATION: Ser(P)

<400> SEQUENCE: 14
```

```
Cys Cys Cys Cys Gly Gly Gly Ser Ser Asp Ser Asp
 1               5                  10
```

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

```
Cys Cys Cys Cys Gly Gly Gly Lys Ile Lys Val Ala Val
 1               5                  10
```

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

```
Tyr Gln Tyr Gln Tyr Gln
 1               5
```

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

```
Ala Gln Ala Gln Ala Gln
 1               5
```

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

```
Tyr Gln Ala Gln Tyr Gln Ala Gln
 1               5
```

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

```
Arg Ala Asp Ala Arg Ala Asp Ala
 1               5
```

<210> SEQ ID NO 20
<211> LENGTH: 6
<212> TYPE: PRT
<213> ORGANISM: Artificial Sequence
<220> FEATURE:

-continued

```
<223> OTHER INFORMATION: Description of Artificial Sequence: Synthetic
      peptide

<400> SEQUENCE: 20

His Asn His Asn His Asn
 1               5

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

His Asn His Gln His Asn Gln His
 1               5

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Cys Ala Ala Gly Gly Gly Lys Arg Gly Asp Ser
 1               5                  10
```

COMPOSITION AND METHOD FOR SELF-ASSEMBLY AND MINERALIZATION OF PEPTIDE AMPHIPHILES

CROSS REFERENCE TO RELATED APPLICATIONS

This application claims the benefit of U.S. Provisional Application No. 60/425,536 filed Nov. 12, 2002, entitled SELF ASSEMBLY OF MULTIDIMENSIONAL PEPTIDE AMPHIPHILES and the benefit of U.S. Provisional Application No. 60/425,689 filed Nov. 12, 2002, entitled COMPOSITION AND METHOD FOR SIMULTANEOUS SELF-ASSEMBLY AND MINERALIZATION OF PEPTIDE-AMPHIPHILES and the benefit of International Application No. PCT/US03/04779 filed Feb. 18, 2003, entitled "SELF-ASSEMBLY OF PEPTIDE-AMPHIPHILE NANOFIBERS UNDER PHYSIOLOGICAL CONDITIONS", the contents of which are incorporate herein by reference in their entirety.

GOVERNMENT INTEREST

The United States government may have certain rights to this invention pursuant to Grant Nos. N00014-99-1-0239/P00001, DMR-9996253, and DE-FGO2-00ER45810 from respectively, the Office of Naval Research, the National Science Foundation, and the Department of Energy to Northwestern University.

BACKGROUND OF THE INVENTION

Self-assembled gels composed of peptide-amphiphile nanofibers have been described as being useful in the templated mineralization of hydroxyapatite. Peptide-amphiphiles enriched with negatively charged amino acids such as phosphoserine and aspartic acid can self assemble into nanofibers and induce hydroxyapatite crystals to grow on the surface of the nanofiber as described by Hartgerink et al., Science, 294, 1683-1688, (2001). In addition to providing sites for hydroxyapatite crystal nucleation, the nanofibers also direct the growth of the hydroxyapatite crystals such that their c-axis is oriented parallel to the long axis of the nanofibers. The ability of the peptide-amphiphile nanofibers to organize and direct the growth of the hydroxyapatite crystals is reminiscent on that observed between collagen fibrils and hydroxyapatite crystals in bone.

The directed growth of hydroxyapatite crystals within organized peptide-amphiphile matrices and scaffolds is an important step toward the regeneration of mineralized materials like bone within the body.

While the preparation of oriented hydroxyapatite crystals on individual or small groups of nanofibers has been demonstrated, scaling the utility of hydroxyapatite or other minerals in bundles of nanofibers or within gels comprising nanofibers maybe limited by non-homogeneous mineralization. Non-homogeneous mineralization of nanofiber bundles or nanofiber gels results in coating of the surface nanofibers of the bundle or gel by the mineral crystals. The formed surface crystals inhibit further diffusion of mineral reagents into the interior of the nanofiber bundle or nanofiber gel and precludes formation of larger homogenous composites. In practical applications such as bone regeneration, it would be desirable that hydroxyapatite crystal growth proceed uniformly throughout the nanofiber gel matrix.

A supramolecular assembly is a material in which the constituent units or building blocks of the assembly are molecules or molecular aggregates. The interaction of the units with each other, usually by non-covalent bonding, determines the final shape and size of the supramolecular assembly. An example of a supramolecular assembly found in biological systems is α-hemolysin which is a seven protein aggregate with a non-symmetric mushroom shape. The α-hemolysin aggregate has a pore or channel that is about 16 Å in diameter, which runs parallel to the aggregate's long axis. The aggressive human pathogen *Staphylocuccus aureus* uses the asymmetric nature of α-hemolysin to implant its stem into the hydrophobic compartment of cell membranes and the hydrophilic nature of the α-hemolysin's mushroom cap to stabilize it in the extracellular space. It is though α-hemolysin's pore channel that RNA macromolecules from the *Staphylocuccus aureus* pathogen can invade human cells. Synthetic supramolecular assemblies could be designed and synthesized to mimic the action of α-hemolysin's channel pore for drug delivery or other cell therapies.

The amino acid sequence IKVAV (SEQ ID NO: 1) has been identified in other contexts as important for neuron growth and development. Self assembly of peptide-amphiphiles with the IKVAV (SEQ ID NO: 1) sequence have been reported. These peptide-amphiphiles may facilitate neuron growth and development in supramolecular structures formed by these peptide-amphiphiles. One feature of peptide-amphiphiles having a hydrophobic alkyl tail and the IKVAV (SEQ ID NO: 1) amino acid sequence in the peptide head group is that peptide-amphiphile has more than one amphiphilic moment. The peptide sequence of these and other peptide-amphiphiles can be further modified by covalent attachment of ligands or peptide sequences that can interact with various types of cells. For example, the peptide sequence Arg-Gly-Asp (RGD) occurs in fibronectin and has been found to play an important role in integrin-mediated cell adhesion. Inclusion of the RGD peptide sequence ligand into a suitable peptide-amphiphile is expected to promote cell growth and direct templated mineralization of self assembled supramolecular structures of such peptide-amphiphiles under the proper conditions. Self assembled peptide-amphiphiles are known to direct the mineralization of hydroxyapatite on the surfaces of nanofibers formed from these peptide-amphiphiles. The peptide portion of these peptide-amphiphiles can also comprise amino acid groups like cysteine, which are capable of forming disulfide bonds between adjacent peptide-amphiphiles, and also glycine which provides flexibility to the peptide portion of the molecule.

It will be appreciated by those skilled in the art that there is a need to be able to form self assembled supramolecular structures from peptide-amphiphiles having more than one amphiphilic moment in order to take advantage of the unique cell growth, molecular transport, and templating functions that these and other related peptide sequences provide. It will also be appreciated that the self assembly occur in physiologically benign conditions of temperature, ionic strength, and pH. For the foregoing reasons, there is a need in the art to make supramolecular assemblies from multi-dimensional peptide-amphiphiles.

The present invention is directed to amphiphilic molecular compositions having more than one amphiphilic moment and also to supramolecular composition comprised of such amphiphilic molecules. More specifically, the present invention is directed to peptide-amphiphiles compositions having more than one amphiphilic moment and to supramolecular compositions comprised of such peptide-amphiphiles which self assemble in the presence of cations.

Preferred embodiments of the present invention may be useful for cell growth, molecular transport, and templating functions, especially if the self assembly occurs under benign conditions.

Homogeneously, or substantially homogeneously, mineralized self assembled peptide-amphiphile nanofibers are desirable. Homogenously mineralized materials with the mineral crystals preferentially oriented by the self assembled peptide-amphiphile nanofibers are also desired. Finally, preparing such materials under substantially neutral or physiological conditions is also desirable.

SUMMARY OF THE INVENTION

One embodiment of the present invention is directed to a composition for material formation on self assembled peptide-amphiphiles comprising at least one ionically charged species of peptide-amphiphile and at least one salt providing at least one ion from the material to be formed and having the same signed ionic charge as the peptide-amphiphile. Alternatively, the composition may be a solution of at least one species of peptide-amphiphile wherein the species of peptide-amphiphile chelates one or more ions of the material to be formed. Charged and chelating peptide-amphiphiles may also be combined to form compositions for self assembly and material formation.

The present invention is directed to a composition for material formation on self assembled peptide-amphiphiles comprising at least one ionically charged species of peptide-amphiphile; and at least one salt providing at least one ion from the material to be formed and having the same signed ionic charge as the peptide-amphiphile.

The invention is also directed to a method of making materials on self assembled peptide-amphiphiles, the method comprises preparing a first solution with at least one ionically charged species of peptide-amphiphile and at least one salt providing at least one ion from the material and having the same signed ionic charge as the peptide-amphiphile. A second solution is prepared with an ion from the material and having opposite signed ionic charge to the peptide-amphiphile in the first solution. The first and second solutions are mixed to cause self-assembly of the peptide amphiphile nanofibers and to form the material substantially on the surfaces of the peptide-amphiphile nanofibers throughout the nanofiber gel.

The present invention is directed to a composition useful for making homogeneously mineralized self assembled peptide-amphiphile nanofibers and nanofiber gels. The composition is generally a first solution comprised of a soluble positively or negatively charged peptide-amphiphile and a soluble salt containing an ion from the mineral. The sign of the charge on the ion in the solution is the same as sign of the charge on the peptide-amphiphile. Mixing this first solution with a second solution containing a dissolved counter-ion of the mineral and/or a second oppositely charged peptide amphiphile, results in the rapid self assembly of the peptide-amphiphiles into a nanofiber gel with templated mineralization on the nanofibers of the salt ions from the solution. Templated mineralization of the initially dissolved mineral cations and anions in the mixture can occur with preferential orientation of the mineral crystals along the fiber surfaces within the nanofiber gel.

One advantage of the present invention is that it results in homogenous growth of the mineral throughout the nanofiber gel. Another advantage of the present invention is that the nanofiber gel formation and mineralization reactions occur in a single mixing step and can occur under substantially neutral or physiological conditions. These homogeneous nanostructured composite materials are useful for medical applications especially the regeneration of damaged bone or teeth in mammals. Non-medical applications of the present invention include the manufacture or coating of hard surfaces on substrates.

In another embodiment of the invention, the composition comprises one or more peptide-amphiphile species having different peptide sequences.

BRIEF DESCRIPTION OF THE FIGURES

Various aspects and applications of the present invention will become apparent to the skilled artisan upon consideration of the brief description of the figures and the detailed description of the invention which follows.

DETAILED DESCRIPTION OF THE INVENTION

Figure 1:
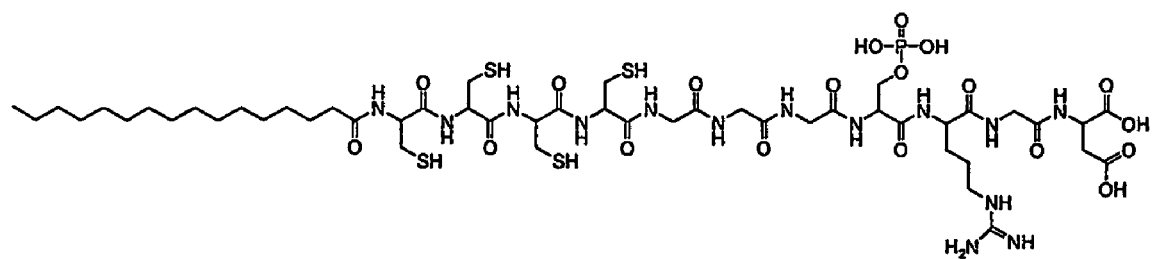
FIG. 1 illustrates the chemical structure of a peptide-amphiphile $C_{15}H_{31}C(O)$-CCCCGGGS(P)RGD-COOH (SEQ ID NO: 2).

As used throughout the specification, the following terms shall have the following meanings, unless the context clearly indicates otherwise. A nanofiber is defined as a cylindrical micelle comprising self-assembled peptide-amphiphiles. Examples of such nanofibers with a single species of peptide-amphiphile are described in *Science,* 294, 1684, (2001). A nanofiber gel comprises a colloidal suspension of self assembled peptide-amphiphile nanofibers and a liquid. The nanofiber gel behaves as an elastic solid and retains its shape. Mineralization is a crystallization process used to describe the nucleation and growth of mineral crystals on the surface of a nanofiber or on the surfaces of nanofibers throughout a nanofiber gel.

Although the present invention will be described in considerable detail with respect to template mediated mineralization of hydroxyapatite on self assembled peptide-amphiphile nanofibers of $C_{15}H_{31}C(O)$-CCCCGGGS(P)RGD-COOH (SEQ ID NO: 2), it is not intended to be limited to this system. Other materials, minerals, biominerals, magnetic materials, conductive materials, and crystals, for example: fluoroapatite, calcium oxalate, calcite, tin hydrogen phosphate, iron oxides, iron hydroxides, and various iron oxyhydroxides, ($Fe_2O_3$, $Fe_3O_4$), $TiO_2$, ZnO, and versions of these materials containing substitutions of the ions, vacancies, or interstitial ions, may be nucleated and grown by the practice of this invention. The invention is not limited by the size of the crystals or crystallites formed on the self assembled peptide-amphiphiles. The formed crystals may be semi-crystalline as well. Numerous positively and negatively charged peptide amphiphile species may be used in this invention, for example $C_{15}H_{31}C(O)$-CCCCGGGS(A)RGD-COOH (SEQ ID NO: 5), as well as those listed in Table 1 and Table 2. Although the present invention is described with respect to aqueous solutions, addition of other liquids or solvents like ethanol to the solution is not precluded in the practice of this invention. The invention may also be practiced by adding an effective amount of the peptide-amphiphile and salts as powders to a surgical site, for example, where fluids containing ions needed for gelation and mineralization may be found.

The peptide-amphiphiles and their self assembled nanofibers may promote adhesion and growth of cells on their surfaces. For example, the cell adhesion ligand RGD has been found in other contexts to play an important role in integrin-mediated cell adhesion. Peptide-amphiphile species with acidic amino acids and an amino acid with the RGD ligand could be used to mediate cell adhesion to the peptide-amphiphiles, their self assembled nanofibers, or nanofiber gels. The amino acid sequence IKVAV (SEQ ID NO: 1) has been identified in other contexts as important for neuron growth and development. Accordingly, peptide-amphiphile species with acidic amino acids and the IKVAV (SEQ ID NO: 1) sequence could be used in the practice of this invention to mediate neuron growth to the peptide-amphiphiles, their self assembled nanofibers, or nanofiber gels. The amino acid sequence YIGSR (SEQ ID NO: 6) has been identified in other contexts as important in for promoting cell-substrate adhesion among nerve cells also to play a role in axon guidance. Accordingly, peptide-amphiphile species with acidic amino acids and the YIGSR (SEQ ID NO: 6) sequence could be used in the practice of this invention to promote cell-substrate adhesion among nerve cells to the peptide-amphiphiles, their self assembled nanofibers, or their nanofiber gels. For example in dentin, the phosphophoryn protein family contains numerous repeats of the amino acid sequences Asp-Ser (P)-Ser(P) and Ser(P)-Asp. These massively phosphorylated proteins are suspected to play an important role in hydroxyapatite mineralization. Accordingly, phosphoserine residues can be incorporated into the peptide sequence which, after self assembly, allows the fiber to display a highly phosphorylated surface equivalent to that presented by a long peptide segment. This, in part, captures the repetitive organization of phosphate groups found in phosphophoryn proteins.

In one embodiment a composition useful in the self assembly and mineralization of peptide-amphiphiles comprises a first solution of at least one negatively charged species of peptide-amphiphile and a soluble salt providing an anion of the mineral. The magnitude of the charges on the peptide amphiphile and anion do not have to be the same. The peptide-amphiphile is prepared using standard solid phase chemistry known to those skilled in the art. The dissolved anion may be obtained from a soluble salt or salts comprising the mineral. Alternatively, the mineral anion is formed by reaction known to those skilled in the art of the salts, for example with the pH adjustment of the solution, to yield the anion of the mineral. In cases where the mineral has more than one anion, a mixture of salts comprising the anions of the mineral may be used. In a preferred embodiment $NaH_2PO_4$ is the source of phosphate ion for the formation of hydroxyapatite. A second solution comprising one or more cations of the mineral obtained from soluble salt or salts is mixed with the first solution resulting in the self assembly of the peptide-amphiphiles into a nanofiber gel. The second solution may optionally contain one or more positively charged peptide-amphiphiles. Templated mineralization of the cations and anions in the mixture occurs within the nanofiber gel formed from the peptide-amphiphiles.

In another embodiment, a composition useful in the self assembly and mineralization of peptide-amphiphiles comprises a first solution of at least one positively charged species of peptide-amphiphile and a soluble salt providing a cation of the mineral. The magnitude of the charges on the peptide amphiphile and cation do not have to be the same. The peptide-amphiphile is prepared using standard solid phase chemistry known to those skilled in the art. The dissolved cation may be obtained from a soluble salt or salts comprising the mineral. Alternatively, the mineral cation is formed by reaction of salts with the pH adjusted solution to yield the cation of the mineral. In cases where the mineral has more than one cation, a mixture of salts comprising the cations of the mineral may be used. A second solution comprising one or more anions of the mineral obtained from soluble salt or salts is mixed with the first solution resulting in the self assembly of the peptide-amphiphiles into a nanofiber gel. The second solution may optionally contain one or more negatively charged peptide-amphiphile. Templated mineralization of the cations and anions in the mixture occurs within the nanofiber gel formed by the peptide-amphiphiles.

In cases where the mineral has more than one cation, a mixture of salts comprising the cations may be mixed with the first solution to yield the homogeneous nanostructured material. The salt may be organic, inorganic, or a peptide-amphiphile. Examples of such cations obtained from salts and useful in the practice of this invention include but are not limited to $NH_4^+$, $Na^+$, $Al^{+3}$, $Fe^{+3}$, $Mg^{+2}$, $Fe^{+2}$, $Ca^{+2}$, $Zn^{+2}$, $Cu^{+2}$, $Gd^{+3}$ and mixtures of these ions. Peptide amphiphiles with a positive charge may be considered as cations for the practice of this invention. Examples of anions useful in the practice of this invention include but are not limited to $PO_4^{-3}$, $AsO_4^{-3}$, $CO_3^{-2}$, $OH^-$, $C_2O_4^{-2}$ silicates, sulfates and mixtures of these and other anions known to those skilled in the art. Peptide amphiphiles with a negative charge may also be considered as anions useful in the practice of this invention.

In another embodiment, the compositions can further comprise mixture of peptide-amphiphiles having the same signed ionic charge, but having different peptide sequences, functional groups, or magnitude of ionic charge. Acidic groups on poly-peptide substrates plays a key role in biomineralization processes. Phosphorylated groups are particularly preferred in this regard.

In another embodiment one or more of the peptide amphiphiles chelates an ion of the material to be formed. The chelating peptide-amphiphile may be neutral or ionically charged. The peptide amphiphile chelating the ion is then mixed with suitable ions or other peptides to form self-assembled nanofiber gels.

Notwithstanding embodiments provided above, broader aspects of the present invention include a peptide amphiphile composition having a hydrophobic or lyophobic component and a lyophilic peptide or peptide-like component. In various preferred embodiments, the hydrophobic component of such a composition is of sufficient length to provide amphiphilic behavior and micelle formation in water or another polar solvent system. Typically, such a component is a $C_6$ or greater hydrocarbon moiety, although other hydrophobic, hydrocarbon and/or alkyl components could be used as would be well-known to those skilled in the art to provide similar functional effect. Examples of such groups include but are not limited to arachidonyl, various length vinylic groups containing substituted with hydrogen or halogens such as fluorine, chlorine, bromine and iodine; acetylenic, diacetylenic and other acetylenic oligomers; various length alkene and isoprene groups substituted with hydrogen or halogens such as fluorine, chlorine, bromine and iodine. Regardless, the peptide component of such a composition can include the aforementioned RGD, IKVAV (SEQ ID NO: 1), or other sequences found especially useful for the nanofiber mineralization described herein.

Preferred peptide components of such compositions can also include a phosphoryl-functionalized residue or sequence, as described above. Inclusion of a phosphoserine residue has been found especially useful for hydroxyapatite mineralization. Other embodiments can include a phosphotyrosine residue. The peptide component of such compositions also include a residue or sequence capable of promoting intermolecular bonding and structural stability of the nanofibers available from such compositions. A sequence of cysteine residues can be used with good effect, providing for the facile intermolecular oxidation/reduction of the thiol functionalities.

Peptide components of this invention preferably comprise naturally-occurring amino acids. However, incorporation of artificial amino acids such as beta or gamma amino acids and those containing non-natural side chains, and/or other similar monomers such as hydroxyacids are also contemplated, with the effect that the corresponding component is peptide-like in this respect. Accordingly, such artificial amino acids, hydroxyacids or monomers can be used to meet the phosphorylation and/or intermolecular bonding objectives described above.

Various aspects of the present invention can be described with reference to the peptide amphiphile illustrated in FIG. 1. Consistent with broader aspects of this invention, other peptide-amphiphiles, for example those listed in Table 1, may be used for the self-assembly of fibrous cylindrical micelles.

TABLE 1

| PA | N-terminus | Peptide (N to C) | C-terminus |
|----|------------|------------------|------------|
| 1 | C16 | CCCCGGGS(P)RGD (SEQ ID NO:2) | COOH |
| 2 | C16 | CCCCGGGS(P) (SEQ ID NO:7) | COOH |
| 3 | H | CCCCGGGS(P)RGD (SEQ ID NO:2) | COOH |
| 4 | C10 | CCCCGGGS(P)RGD (SEQ ID NO:2) | COOH |
| 5 | C6 | CCCCGGGS(P)RGD (SEQ ID NO:2) | COOH |
| 6 | C10 | GGGS(P)RGD (SEQ ID NO:8) | COOH |
| 7 | C16 | GGGS(P)RGD (SEQ ID NO:8) | COOH |
| 8 | C16 | AAAAGGGS(P)RGD (SEQ ID NO:9) | COOH |
| 9 | C10 | AAAAGGGS(P)RGD (SEQ ID NO:9) | COOH |
| 10 | C16 | CCCCGGGS(P)KGE (SEQ ID NO:10) | COOH |
| 11 | C10 | AAAAGGGS(P)KGE (SEQ ID NO:11) | COOH |
| 12 | C16 | AAAAGGGS(P)KGE (SEQ ID NO:11) | COOH |
| 13 | C22 | CCCCGGGS(P)RGD (SEQ ID NO:2) | COOH |
| 14 | C16 | CCCCGGGSRGD (SEQ ID NO:12) | COOH |
| 15 | C16 | CCCCGGGEIKVAV (SEQ ID NO:3) | COOH |

TABLE 1-continued

| PA | N-terminus | Peptide (N to C) | C-terminus |
|----|------------|------------------|------------|
| 16 | C16 | CCCCGGGS(P)RGDS (SEQ ID NO:13) | COOH |
| 17 | C16 | CCCCGGGSS(P)D(S(P)D (SEQ ID NO:14) | COOH |

It should be noted that within the system examined, PAs 3 and 5 do not exhibit micelle formation, demonstrating a certain degree of hydrophobicity required for self-assembly of such compositions into the nanofibers of this invention. Depending upon desired cell or mineral growth, a phosphorylated moiety may not be required (see PAs 14 and 15). As discussed above, cellular adhesion or interaction is promoted by a particular sequence of the peptide components. With reference to PA's 10-12 and 15, a non-RGD sequence can be utilized depending upon cellular target. In particular, the IKVAV (SEQ ID NO: 1) sequence has been identified in other contexts as important for neuron growth and development. Accordingly the amphiphile compositions of this invention can include a peptide component having such a sequence for corresponding use. Lastly, with respect to Table 1, it is noted that several PA compositions do not include cysteine residues: while such a peptide sequence can be used to enhance intermolecular nanofiber stability, it is not required for micelle formation in the first instance.

In part, the present invention also provides for a system including an aqueous solution of one or more of the amphiphile compositions described herein, and a factor or reagent sufficient to induce gelation under physiological conditions. Such gelation and/or self-assembly of various PA compositions into cylindrical micelle nanofibers can be achieved under substantially neutral pH conditions through drying, introduction of monovalent, divalent, or higher valency ions and/or the combination of differently charged amphiphiles. The approach of using differently charged amphiphiles can also be utilized to deliver in the self assembling nanofibrous system two or more bioactive molecules, each bearing different charges and this way combining the gelation technology with the delivery of multiple biological signals. Such facile factors, as described more fully below and in several of the following examples, can extend the system and/or methodology of this invention to a variety of medical applications. These and other aspects of the present invention can be described with reference to the peptide-amphiphile, PA, compositions provided in Table 2, and with further reference to FIG. 1 and Table 1.

TABLE 2

| PA | N-terminus | Peptide (N to C) | C-terminus | Net Charge at pH 7 |
|----|------------|------------------|------------|--------------------|
| 18 | C16 | CCCCGGGS(P)RGD (SEQ ID NO:2) | COOH | −3 |
| 19 | C16 | AAAAGGGS(P)RGD (SEQ ID NO:9) | COOH | −3 |
| 20 | C10 | AAAAGGGS(P)RGD (SEQ ID NO:9) | COOH | −3 |
| 21 | C16 | CCCCGGGSRGD (SEQ ID NO:12) | COOH | −1 |
| 22 | C16 | CCCCGGGEIKVAV (SEQ ID NO:3) | COOH | −1 |
| 23 | C16 | CCCCGGGKIKVAV (SEQ ID NO:15) | COOH | +1 |

In another embodiment of the invention, the degree of mineralization or crystallization is controlled. By modifying the degree of crystallization, control of the physical properties of the peptide-amphiphile mineral composite is achieved. The method comprises aging the mixture of the first and second solutions to control the extent of the mineralization and crystal growth reaction. Crystal growth requires, among other variables, control of the temperature and contact time of the mixture containing the cations and anions with the nanofiber gel.

As stated above, the amphiphile composition(s) of such a system may include a peptide component having residues capable of intermolecular cross-linking. The thiol moieties of cysteine residues can be used for intermolecular disulfide bond formation through introduction of a suitable oxidizing agent or under physiological conditions. Conversely such bonds can be cleaved by a reducing agent introduced into the system or under reducing conditions. The concentration of cysteine residues can also be varied to control the chemical and/or biological stability of the nanofibrous system and therefore control the rate of therapeutic delivery or release of cells or other beneficial agent, using an effective amount of the nanofibers as the carriers. Furthermore, enzymes could be incorporated in the nanofibers to control biodegradation rate through hydrolysis of the disulfide bonds. Such degradation and/or the concentration of the cysteine residues can be utilized in a variety of tissue engineering contexts.

The ability of various peptide sequences in the peptide-amphiphiles to promote bone, tissue, or nerve growth may make systems of self assembled nanofibers useful in a number of different potential application. Specific applications include the delivery of therapeutics as well as biomedical and tissue engineering. As a self-supporting gel, it may have applications as a mineralizable bone-defect filler.

The assembly in the presence of biological ions such as $Ca^{2+}$ may make the homogeneously mineralized material herein described particularly valuable for in situ and in vivo applications. It may also be used as a biological coating for orthopedic implants. These applications could find particularly valuable use in addressing medical problems such as osteooncology, congenital bone and tooth defects, osteoporosis, synthetic teeth, and dental implants.

The self-assembled peptide amphiphiles described in this disclosure are modifications of those originally described by Hartgerink, et al. (See e.g., J. D. Hartgerink, E. Beniash and S. I. Stupp, *Science* 294, 1683-1688, 2001), which is hereby incorporated in its entirety by reference thereto and the synthetic schemes set forth therein apply actually as well to the present invention.

Self-assembly and/or gelation under physiological conditions raises numerous implication regarding the end-use application and effect. A peptide-amphiphile mixture makes available a system for the formation of micellular nanofibers in an aqueous environment at neutral and/or physiological pH conditions. Such a combination can be used to assemble nanofibers with a range of chemical groups or amino acids providing a variety of chemical or biological signals for corresponding cell adhesion, yielding enhanced properties with respect to tissue engineering or regenerative applications. It is contemplated that, alone or in conjunction with the other factors discussed herein, that preferred medical or therapeutic embodiments of such a system can be utilized. Furthermore, although the invention will be described in detail with respect to aqueous solution, the presence of non-aqueous liquids in the solution, like ethanol, will not limit the scope of the invention. Similarly, use of the terms hydrophobic and hydrophilic to describes the interaction of the multi-dimensional amphiphiles with water are construed to be equivalent to lyophobic and lyophilic for interaction of the multidimensional amphiphiles with non-aqueous liquids.

Figure 5:
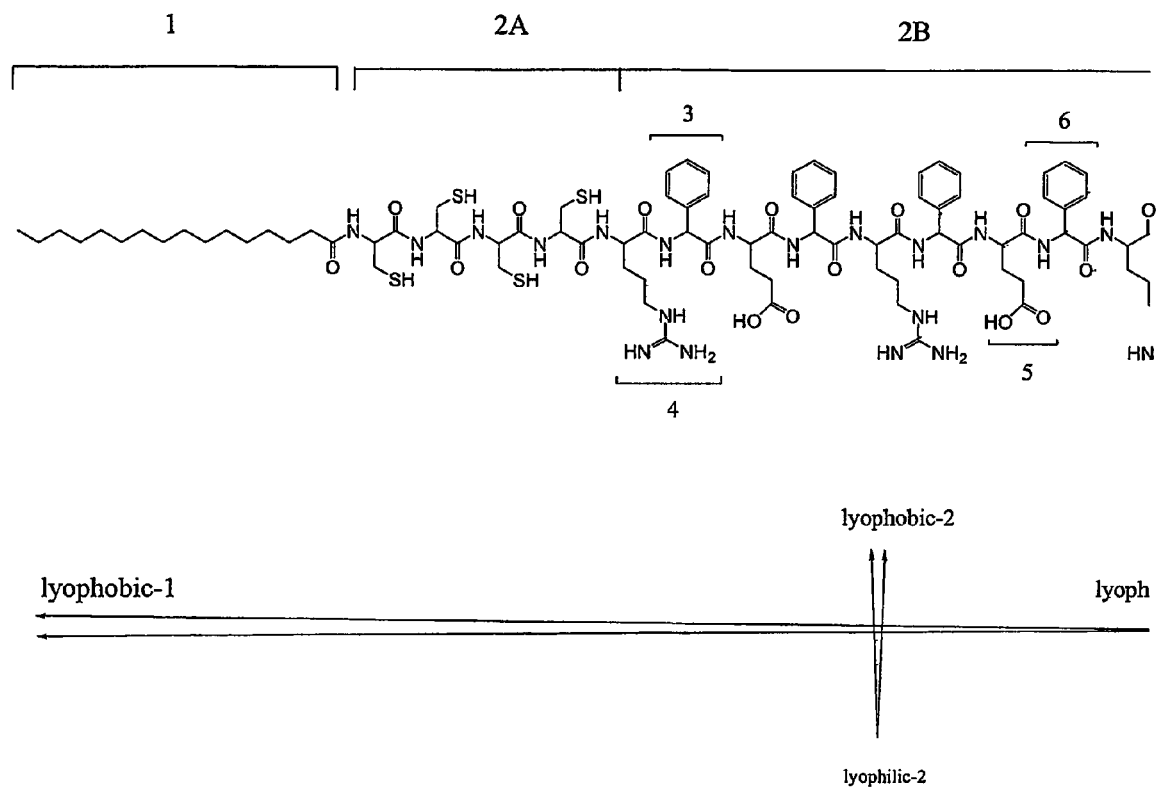
FIG. 5 is a schematic drawing of the chemical structure of the peptide-amphiphile $C_{15}H_{31}C(O)$-CCCCRFEFRFEFR-$NH_2$ illustrating the important groups of the molecule as well as a representation of the magnitude and direction of two of the amphiphilic moments in the molecule. For illustrative purposes, Region 1 may be an alkyl group that is covalently bonded to Region 2, which may be divided further into sections 2A and 2B, Regions 1 and 2 together define a first amphiphilic moment of the molecule. The molecule may further comprise a second amphiphilic moment defined by Regions 2A and 2B, wherein Region 2B comprises the polar and non-polar amino acids labeled 3, 4, 5 and 6.

The present invention is directed to amphiphilic molecular compositions having more than one amphiphilic moment and also to supramolecular composition comprised of such amphiphilic molecules. An amphiphilic molecule with more than one amphiphilic moment is referred to as a multi-dimensional amphiphile. An example of such a molecule is shown schematically in FIG. 5. The multi-dimensional amphiphilic molecule has a first chemical group or moiety, 1, covalently bonded to a second chemical group or moiety. In FIG. 5 the second moiety is further divided into sections 2A and 2B. In FIG. 5, and for illustrative purposes only, the second chemical moiety is a peptide comprised of amino acids. The amino acids may be, for example, naturally occurring amino acids, synthetic amino acids, β-amino acids, γ-amino acids, and or mixtures of these amino acids. The first and second moieties define a first amphiphilic moment of the amphiphilic molecule. The direction and magnitude of the first amphiphilic moment is along the axis of the molecule and is represented by divergent lines and labels lyophobic-1 and lyophilic-1 in FIG. 5.

The second moiety of the molecule is further comprised of moieties covalently bonded together that define a second amphiphilic moment of the molecule. In FIG. 5, for example, the second moiety is a peptide comprised of cysteine amino acids (2A) and polar and non-polar amino acids labeled 3, 4, 5, and 6. The amino acid moieties 4 and 5 are polar and substantially lyophilic because of the nature of the substituents. Examples of these substituents may be, acid groups, amine and amide groups, phosphate groups, hydroxyl groups, and sulfate groups, and carboxylic acid groups. The amino acid moieties 3 and 6 are the same in this example, but they may be different, and are non-polar and substantially lyophobic because of the nature of the substituents. Examples of these substituents may be phenyl, methyl, or substituted alkyl groups. The sequence of polar/lyophilic and nonpolar/lyophobic moieties that make up the second lyophilic moiety in the molecule defines a second amphiphilic moment in the molecule. The second amphiphilic moment is not parallel to the first amphiphilic moment of the molecule. In FIG. 5 the direction and magnitude of the second amphiphilic moment lies or is oriented across the first amphiphilic moment of the molecule; the two moments are not parallel to each other. The second amphiphilic moment is represented by the smaller divergent lines and labels lyophobic-2 and lyophilic-2 in FIG. 5. A molecule with more than one amphiphilic moment is termed a multi-dimensional amphiphile; a molecule with more than one amphiphilic moment and having a peptide is termed a multidimensional peptide-amphiphile.

The portion of the peptide sequence labeled 2A in FIG. 5 has cysteine amino acids capable of bonding together adjacent multidimensional peptide-amphiphiles in a self assembled nanofiber. In the molecule depicted in FIG. 5, the cysteine amino acids may be replaced with glycine amino acids to provide flexibility to the peptide portion of the molecule. The cysteine amino acids may be replaced with other polar or non-polar amino acids. Other synthetic amino acids, b-amino acids, g-amino acids with polar or non-polar substituents may be used in the practice of this invention. Incorporation monomers such as hydroxyacids are also contemplated, with the effect that the corresponding component is peptide-like in this respect. The sequence of alternating polar and non-polar moieties and more specifically the alternating polar and non-polar amino acids may be varied and the invention is not limited to disclosed combinations. The peptide may contain the amino acid sequence IKVAV (SEQ ID NO: 1). Other examples of peptides with alternating hydrophobic and hydrophilic amino acids, include but are not limited to: YQYQYQ (SEQ ID NO: 16); AQAQAQ (SEQ ID NO: 17); YQAQYQAQ (SEQ ID NO: 18); RADARADA (SEQ ID NO: 19); HNHNHN (SEQ ID NO: 20); HNHQHNQH (SEQ ID NO: 21).

This invention is more specifically directed to the synthesis of peptide-amphiphiles with more than one amphiphilic moment and to supramolecular compositions comprised of such multi-dimensional peptide-amphiphiles. These supramolecular compositions can be formed by self assembly of multi-dimensional peptide-amphiphiles by mixing them with a solution comprising a cation. In a preferred embodiment monovalent cations are used to induce self assembly of the multidimensional peptide-amphiphiles. Examples of such cations include but are not limited to $Na^+$, $K^+$, or $RNH_3^+$, where R is a hydrogen, a phenyl group, or an alkyl group.

In a preferred embodiment of the invention, a supramolecular composition is formed by mixing multi-dimensional peptide-amphiphiles containing the IKVAV (SEQ ID NO: 1) amino acid sequence with a monovalent cation from salts such as NaCl and KCl. Examples of suitable multi-dimensional peptide amphiphiles are Molecule 1 and Molecule 2 illustrated in FIG. 3. The peptide-amphiphile has amino acids with moieties for covalent coupling. Examples of such amino acids include but are not limited to cysteine. The peptide-amphiphile also has amino acids that provide a flexible linkage within the peptide portion of the molecule. Examples of such amino acid moieties include but are not limited to gylcine.

More specifically, the peptide-amphiphiles of this invention contain a hydrophobic or lyophobic component of sufficient length to provide amphiphilic behavior and micelle formation in water or polar solutions. Typically, such a first moiety is a $C_6$ or greater hydrocarbon group, although other hydrocarbon and/or alkyl components could be used in place of or bonded as a substituents onto the hydrocarbon group as would be well known to those skilled in the art. Examples of such groups include but are not limited to arachidonyl, various length vinylic groups containing substituted with hydrogen or halogens such as fluorine, chlorine, bromine and iodine; acetylenic, diacetylenic and other acetylenic oligomers; various length alkene and isoprene groups substituted with hydrogen or halogens such as fluorine, chlorine, bromine and iodine.

The invention may also be practiced by adding an effective amount of the peptide-amphiphile and salts as powders to a surgical site, for example, where fluids containing ions needed for gelation and mineralization may be found.

The self assembly and gelation of peptide-amphiphiles like Molecule 1 and Molecule 2 to form the supramolecular composition is triggered by addition of monovalent cations into the peptide-amphiphile solution. The monovalent salts provide an ionic environment that is believed to reduce the electrostatic repulsive force between peptideamphiphiles of the same polarity. Examples of suitable monovalent cations include but are not limited to $Na^+$, $K^+$, or $RNH_3^+$. The monovalent cations in solution enable the peptideamphiphiles to establish short range hydrophobic interactions between the aliphatic tails of the molecules as well as the amphiphilic portions of the peptide sequence. Amphiphilic peptides were previously reported to self assemble into β-sheet based supramolecular structures (Aggeli et. al. 1977, and Holmes et al., 2000).

One advantage of the present invention is that the peptide amphiphiles self assemble to form fibers rather hollow tubes. Such fibers may be suitable for deliver or encapsulation of various cell therapies and provide close surfaces for templated tissue, bone, or nerve growth. The delivery of an effective amount of such encapsulated therapeutics to a patient may be useful in the treatment of a variety of conditions. The structure of the peptide-amphiphile may be changed to create self assembled structures having various pore sizes. Although the present invention will be described in considerable detail with respect to self assembly of multi-dimensional peptide amphiphiles with the IKVAV (SEQ ID NO: 1) peptide and their use in promoting cell growth, it is not intended to be limited to this amino acid sequence or to cell growth. Other multi-dimensional peptide amphiphiles with alternating polar and non-polar amino acids sequences may self assemble and direct the growth of tissues, materials, minerals, biominerals, magnetic materials, conductive and semiconductor materials, and crystals on their surfaces. Examples of such materials include but are not limited to fluoroapatite, calcium oxalate, calcite, tin hydrogen phosphate, iron oxides, iron hydroxides, and various iron oxyhydroxides, ($Fe_2O_3$, $Fe_3O_4$), $TiO_2$, ZnO. Versions of these materials containing substitutions of the ions, vacancies, or interstitial ions, may also be nucleated and grown by the practice of this invention. The invention is not limited by the size of the crystals or crystallites formed on the self assembled peptide-amphiphiles. The formed crystals may be semi-crystalline as well.

Another difference between the peptide-amphiphiles in the present invention from known amphiphilic molecules is that the present invention's peptide-amphiphiles are two-dimensional amphiphiles. The peptide-amphiphiles of the present invention have two "amphiphilic moments" oriented in different directions. One amphiphilic moment coincides with or is parallel to the backbone axis of the molecule, the second amphiphilic moment is not parallel to the backbone of the molecule and is directed across the peptide sequence of the molecule. The alkyl tail moiety of the peptide-amphiphile is much more hydrophobic than any moieties on the amino acids composing the peptide part of the peptide-amphiphile. The amphiphilic moment along the backbone of the peptide-amphiphile molecule is much stronger than the amphiphilicity across the IKVAV (SEQ ID NO: 1) segment. The amphiphilicity in different directions is different; it is much stronger along the backbone of the molecule than along the sides of the amphiphilic peptide segment. This molecular design may serve as a prototype for other multi-dimensional amphiphilic molecules, which may not include the peptide or alkyl moieties. In principle any molecule with two or more axes of amphiphilicity may be described as a multi-dimensional amphiphile. Multi-dimensional amphiphiles can serve as the building blocks for supramolecular assemblies and lead to the development of new supramolecular structures that may find application in different fields of nanotechnology and biomedical applications.

Supramolecular compositions formed from self assembled multi-dimensional amphiphiles may be administered to treat a patient. For example, the patient may require assistance stimulating cell or nerve growth. The treatment comprises administering a multi-dimensional peptide-amphiphile composition having a cell growth peptide sequence within the peptide-amphiphile to a site on the patient requiring treatment. The supramolecular composition may form using sodium or potassium ions already present in the patient. Alternatively a separate solution containing monvalent ions may be administered to the patient to cause the formation of the supramolecular composition from the multi-dimensional peptide-amphiphile solution.

Synthetic supramolecular assemblies could also be designed and synthesized with channels or pores for targeted delivery of drugs to specific cells or organs. These supramolecular assemblies may provide for encapsulation of materials and molecules such as therapeutic drugs, cell therapies, cancer treatments, antibodies, magnetic colloids, conductive colloids, carbon nanotubes, and semiconductor colloids.

EXAMPLE 1

This example illustrates the components of a liquid composition and its use to form homogeneously distributed, and directionally orientated hydroxyapatite crystals within a nanofiber gel comprised of self assembled peptide-amphiphiles.

Peptide amphiphile $C_{15}H_{31}C(O)$-CCCCGGGS(P)RGD-COOH (SEQ ID NO: 2) (1) was prepared using standard solid phase chemistry; its structure is shown in FIG. 1.

A liquid composition for the self assembly of (1) and mineralization of hydroxyapatite was prepared by dissolving 20 millimoles $NaH_2PO_4$ (Aldrich) into 200 microliters of (1) at a concentration of 10 mg/ml in water. The pH of the solution was adjusted to 7.7.

The liquid composition containing (1) and $NaH_2PO_4$ was mixed with 40 micromoles of $CaCl_2$ (Aldrich).

Figure 2:
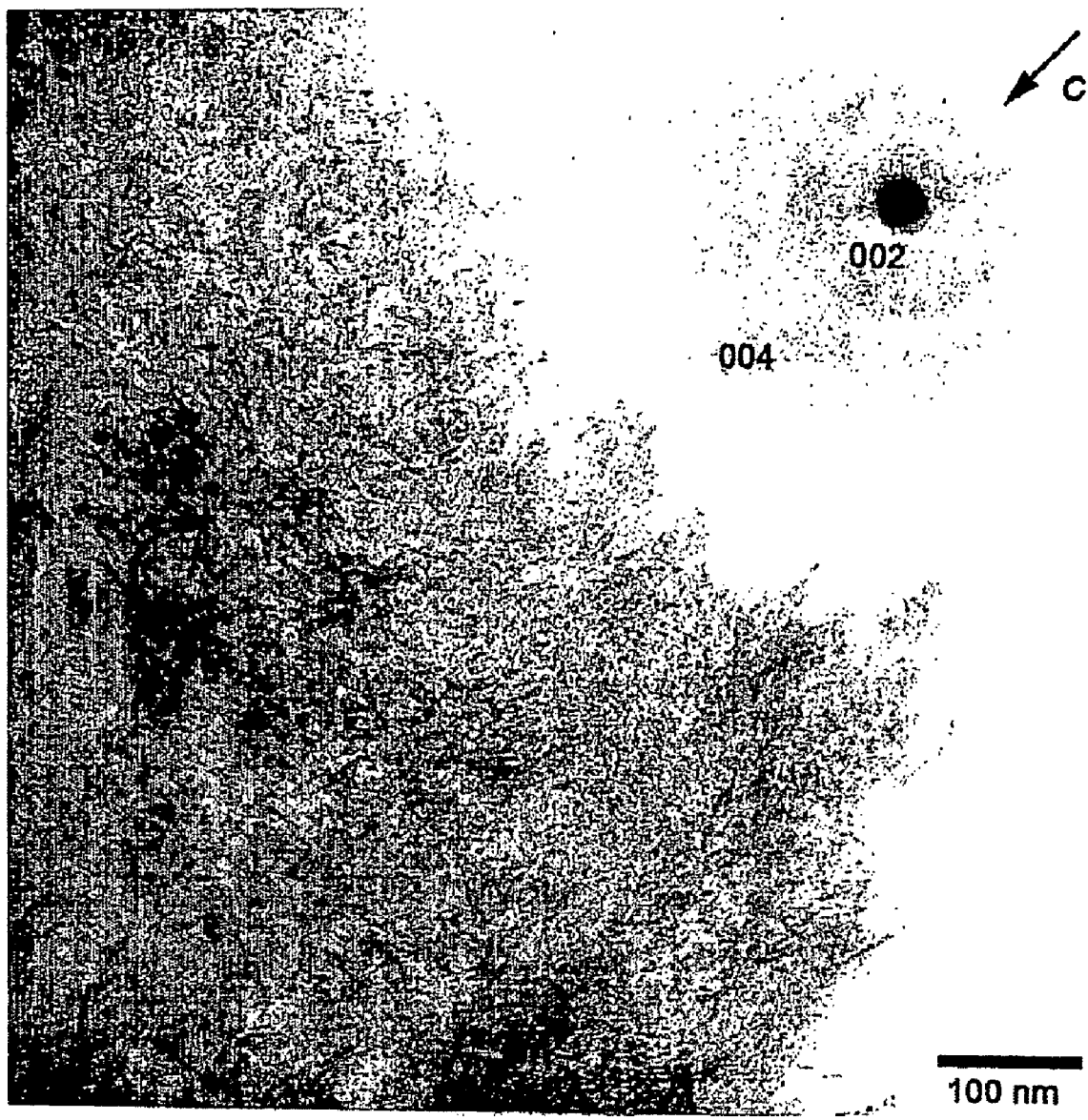
FIG. 2 illustrates a transmission electron micrograph (TEM) of a homogeneously mineralized nanofiber gel sample with oriented hydroxyapatite mineral growth.

Self assembled gel comprising (1) was formed immediately upon addition of $CaCl_2$ to the liquid composition of the peptide-amphiphile (1) preloaded with a source phosphate anions from the $NaH_2PO_4$. The self assembled gel was initially transparent but turned a white color after about 2 hours suggesting that the mineralization process had started. Samples of the gel after 2 hours, 1 day, and 5 days were mounted on carbon-coated TEM grids. TEM studies of the 1 and 5 day samples show a multi-crystalline material composed of plate like crystals ~5 nm thick and 50 to 100 nm long. The plate like crystals were similar to those observed in the mineralization experiments on the pre-assembled template. Electron diffraction of the material matches the diffraction pattern for hydroxyapatite. Both TEM images of the mineralized gel as well as diffraction patterns suggest local orientation of the hydroxyapatite crystals in the self assembled gel. These data suggest that the c-axis of the hydroxyapatite crystals is co-aligned with the nanofiber axis as shown in FIG. 2. This observation suggests that the peptide-amphiphile nanofibrils control nucleation and direction of the crystal growth.

The results of this example show that peptide-amphiphile organo-mineral composite materials may be manufactured in one step by adding metal ions to a liquid composition of peptide-amphiphile pre-loaded with a source of phosphate anions. The example further illustrates that the self-assembly of the peptide-amphiphiles occurs upon addition of a metal ion and that they later serve as a template for the directed mineralization of hydroxyapatite. This example further illustrates that the method for making the hydroxyapatite composites is useful for preparing homogenous nanostructured composite materials.

EXAMPLE 2

In another example of this invention, the composition and method consists of using highly charged peptide amphiphile species (16carbon alkyl tail with a sequence like CCCCGGGSS(P)DS(P)D (SEQ ID NO: 14) with a −7 charge, for example) dissolved in a solution of negative ions (phosphate ions with a −3 charge), call this solution X. A second solution with a positively-charged peptide amphiphile species (such as 16 carbon alkyl tail with a sequence like ACAAGGGKRGDS (SEQ ID NO: 21)—an amine terminated PA at +1 charge) in a solution with positively-charged ions, such as $Ca^{2+}$; call this solution Y. In both solutions the peptide heads are charged and the structural element of the peptide can be varied, to give different charged peptide-amphiphile species, depending on the application.

The positive and negative peptide amphiphiles alone (no added salt ions) will gel each other, reaction 1, when mixed in the right ionic ratios(1:7, (−):(+) in this instance), forming mixed peptide amphiphile nanofibers, theoretically composed of 7 positive peptide amphiphiles for every 1 of the negative peptide amphiphiles. The positive peptide amphiphile solution Y may be gelled, reaction 2, with the negative ions (for example a solution containing phosphate ion $PO_4^{-3}$). The negative peptide amphiphile solution X will be gelled, reaction 3, with positive ions (for example a solution containing $Ca^{+2}$). The positive peptide amphiphile does not gel, reaction 4, in positive ions (for example $Ca^{-2}$) The negative PA does not gel, reaction 5, in negative ions (for example phosphate ion $PO_4^{-3}$). Mixing the positive and negative ions (calcium cation with phosphate anion) will make calcium phosphate mineral (reaction 6). When solution X is mixed with solution Y, a gel forms, reaction 7, very quickly. It is believed that mineral (calcium phosphates and possibly sodium chloride) is nucleated and grown intimately and substantially throughout the mixed-peptide amphiphile fibers. The gel formed may be the product of reactions 1, 2, 3, and 6, occurring in approximately the same time frame. The combination allows us formation of a mineralized gel at physiologic pH. This example further demonstrates that by using two distinct peptide-amphiphiles, different peptide sequences which might work well in concert with one-another (such as IKVAV (SEQ ID NO: 1) and YIGSR (SEQ ID NO: 6)) might be simultaneously combined during the assembly and mineralization process.

EXAMPLE 3

This example describes the synthesis of peptide-amphiphiles with more than one amphiphilic moment, and describes the synthesis of a supramolecular composition comprised of self-assembled multi-dimensional peptide-amphiphiles. A supramolecular composition is formed by combining multi-dimensional amphiphiles containing the IKVAV (SEQ ID NO: 1) amino acid sequence with monovalent salts such as NaCl and KCl.

Figure 3:
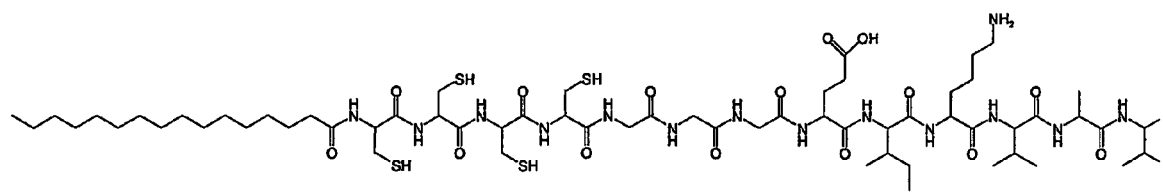
FIG. 3 is a schematic drawing of the chemical structures of the peptide-amphiphiles $C_{15}H_{31}C(O)$-CCCCGGGEIKVAV-COOH (SEQ ID NO: 3), Molecule 1, and $C_{15}H_{31}C(O)$-CCCCGGGEIKVAV-$NH_2$ (SEQ ID NO: 3), Molecule 2.
Figure 3:
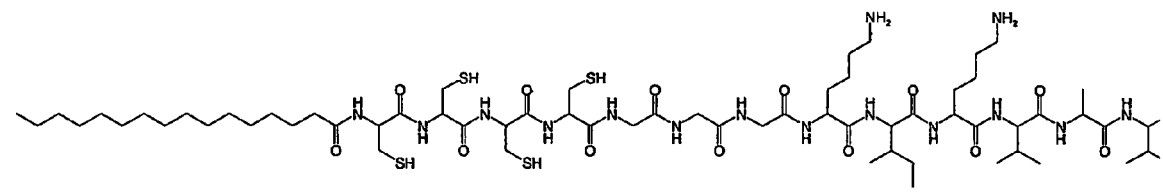
Figure 4:
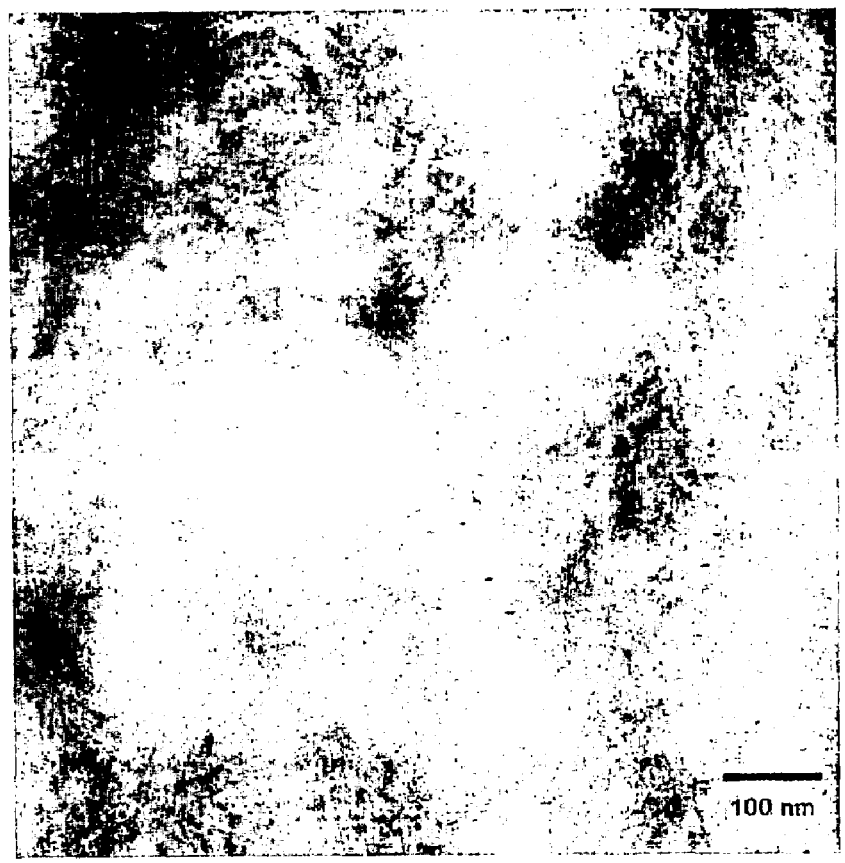
FIG. 4 is a TEM micrograph of the negatively charged peptide-amphiphile nanofibers of molecule 1 self-assembled in the presence of KCl.

Molecule 1, as shown in FIG. 3, is a peptide-amphiphile that contains the amino acid sequence IKVAV (SEQ ID NO: 1) moiety with terminal end group —COOH; this sequence has been shown to promote axon outgrowth in neurons. Molecule 2, also shown in FIG. 3, is a peptide-amphiphile that contains the sequence IKVAV (SEQ ID NO: 1) moiety with the terminal end group—$NH_2$, which has similarly been shown to promote axon outgrowth in neurons. The two molecules dissolve in pH 7.5-adjusted water at a concentration of about 10 mg/mL. Molecule 1 has a charge of (−1) and molecule 2 has a charge of (+2) under these conditions. A self-supporting gel forms on mixing of either of the peptide-amphiphile solutions with 200 mM KCl or NaCl solutions. Examination of the gels formed by these reactions by negative stain TEM shows that the gels are composed of nanofibers of the self assembled peptide-amphiphiles.

In all cases self assembled gels comprised of the nanofibers were formed similar to those described elsewhere (Hartgerink et al., 2001; Hartgerink et al., 2002). In contrast no self assembly or gel formation was observed when other negatively or positively charged peptide-amphiphiles were exposed to the NaCl or the KCl at concentrations up to 6 M.

The fact that molecules 1 and 2 assemble in the presence of the monovalent salts sets them apart from the other molecules studied. Experiments with negatively charged molecules that do not contain amphiphilic peptide sequences show that the charge screening by monovalent inorganic ions alone is not sufficient to induce peptide-amphiphile self-assembly. The reason for this difference may be in the structure of these molecules. Both these molecules contain IKVAV (SEQ ID NO: 1) sequence at the c-terminus of the peptide segment. This sequence is comprised of alternating extremely hydrophobic amino acids I and V and more hydrophilic ones such as A and K. Since the side chains of adjacent amino acids are located on opposite sides of the peptide backbone, this sequence is amphiphilic. The molecules 1 and 2 may be considered as double or two dimensional amphiphiles; one moment of amphiphilicity coinciding with the backbone axis of the molecule and amphiphilic peptide segment at c-terminus, and the second moment of amphiphilicity directed across the amphiphilic peptide segment. Previously amphiphilic peptides have been shown to assemble into ribbon like structures forming 3-D networks upon addition of monovalent salts (Zhang et al., 1995; Caplan et al., 2000). It was suggested that the function of inorganic ions in these systems is to screen charged functional groups of the peptide that facilitates supramolecular assembly of amphiphilic peptides. It is believed that a similar mechanism is involved in the self assembly of peptide-amphiphiles containing IKVAV (SEQ ID NO: 1) sequences in addition to the hydrophobic interactions between the alkyl parts of the molecules.

Materials and Methods: Abbreviations: PA: peptide-amphiphile, TEM: transmission electron microscopy.

Chemicals: Except as noted below, all chemicals were purchased from Fisher or Aldrich and used as provided. Amino acid derivatives were purchased from Applied Bio-Systems and NovaBiochem; derivatized resins and O-Benzotriazole-N,N,N',N'-tetramethyl-uronium-hexafluoro-phosphate (HBTU) were also purchased from NovaBiochem. All water used was deionized with a Millipore Milli-Q water purifier operating at a resistance of 18 MW.

Synthesis of the peptide-amphiphiles: The peptide-amphiphiles were prepared on a 0.25 mmole scale using standard FMOC chemistry on an Applied Biosystems 733A automated peptide synthesizer. After the peptide portion of the molecules was prepared, the resin was removed from the automated synthesizer and the N-terminus capped with a fatty acid containing 16 carbon atoms. The alkylation reaction was accomplished using 2 equivalents of the fatty acid, 2 equivalents HBTU and 6 equivalents of n,n-diisopropylethylamine (DiEA) in dimethylformamide (DMF). The reaction was allowed to proceed for at least six hours after which the reaction was monitored by ninhydrin. The alkylation reaction was repeated until the ninhydrin test was negative. Only two couplings were required in each case.

Cleavage and deprotection of the molecules was accomplished with a mixture of trifluoroacetic acid (TFA) and tri-isopropylsilane (TIS) in a ratio of 95:5 for three hours at room temperature. The cleavage mixture and two subsequent TFA washings were filtered into a round bottom flask. The solution was roto-evaporated to a thick viscous solution. This solution was triturated with cold diethylether. The white precipitate was collected by filtration, washed with copious cold ether and dried under vacuum. The molecules were then dissolved in water at a concentration of 10 mg/mL, adjusting the pH to improve solubility. The solution was initially acidic in both cases. In the case of molecule 1, the pH was raised to about pH 8 with 2M and 100 nM KOH, then back-titrated to pH 7. In the case of molecule 2, the molecule was most soluble at low pH, but remained in solution when the pH was raised to 7 using KOH. The molecules were characterized by ESI MS and were found to have the expected molecular weight.

Transmission Electron Micrographs of samples of the supramolecular compositions from the multi-dimensional peptide-amphiphiles, Molecule 1 and Molecule 2, were prepared as follows. A small sample of the supramolecular composition gel, prepared in bulk as described above, was smeared onto a holey carbon coated TEM grid (Quantifoil). Negative staining with PTA (phosphotungstic acid) was used in this study[Harris, 1991#93]. In all cases electron microscopy was performed at an accelerating voltage of 200 kV.

Various other amphiphile compositions of this invention can be prepared in analogous fashion, as would be known to those skilled in the art and aware thereof, using known procedures and synthetic techniques or straight-forward modifications thereof depending upon a desired amphiphile composition or peptide sequence.

All of the embodiments disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention.

While the principles of this invention have been described in connection with specific embodiments, it should be understood clearly that these descriptions are added only by way of example and are not intended to limit, in any way, the scope of this invention. For instance, various peptide amphiphiles have been described in conjunction with specific residues and corresponding cell adhesion, but other residues can be used herewith to promote a particular cell adhesion and tissue growth on the nanostructures prepared therefrom. Likewise, while the present invention has been described as applicable to biometric material or tissue engineering, it is also contemplated that gels or related systems of such peptide amphiphiles can be used as a delivery platform or carrier for drugs, cells or other cellular or therapeutic material incorporated therein. Other advantages and features will become apparent from the claims filed hereafter, with the scope of such claims to be determined by their reasonable equivalents, as would be understood by those skilled in the art.

REFERENCES

Aizenberg, J.; Black, A. J.; Whitesides, G. M. *Nature,* 398, 495-498, (1999).

Braun, P. V.; Stupp, S. I. *Materials Research Bulletin,* 34, 463-469, (1999).

Hartgerink et al; *Science,* 294, 1684-1688, (2001).

Hartgerink et al, *PNAS,* 99(8), 5133-5138, (2002).

Preparation of self-assembling amphiphile for construction of peptide secondary structures. G. B. Fields, M. V. Tirrell, U.S. Pat. No. 6,096,863.

M. R. Caplan, P. N. Moore, S. G. Shang, R. D. Kamm, D. A. Lauffenburger, *Biomacromolecules;* 1, 627, (2000).

A. L. Litvin, S. Valiyaveettil, D. L. Kaplan Process for nucleation of ceramics and products thereof. U.S. Pat. No. 5,993,541

Xu, G. F. et al, *Journal of the American Chemical Society* 120, 11977-11985, (1998)

What is claimed is:

1. A method for the mineralization of nanofibers, the method comprising:
   preparing a first solution with at least one peptide amphiphile comprising a $C_6$ or greater hydrocarbon component at its N-terminus and a lyophilic peptide component;
   preparing a second solution of a mineral salt; and
   mixing said first and second solutions to self-assemble said peptide amphiphiles into nanofibers and a nanofiber gel, wherein said mineralization occurs from initially dissolved mineral cations and anions along the nanofibers surfaces, wherein said nanofibers are fibrous cylindrical micelles.

2. The method claim 1 further comprising: aging the mixture of said first and second solutions to control the size and rate of growth of said minerals on the self-assembled peptide amphiphile nanofibers.

3. The method of claim 1 further comprising: adjusting the pH of one of the solutions prior to mixing them together.

4. The method of claim 1, wherein said mineral cations and anions are selected from the group consisting of hydroxyapatite, fluoroapatite, calcium oxalate, calcite, tin hydrogen phosphate, iron oxides, iron hydroxides, iron oxyhydroxyoxides, titanium dioxide, and zinc oxide.

5. The method of claim 1, wherein the peptide-amphiphile has a net negative charge.

6. The method of claim 4, wherein the mineral is hydroxyapatite.

* * * * *

UNITED STATES PATENT AND TRADEMARK OFFICE
CERTIFICATE OF CORRECTION

PATENT NO. : 7,554,021 B2  Page 1 of 1
APPLICATION NO. : 10/534097
DATED : June 30, 2009
INVENTOR(S) : Samuel I. Stupp et al.

It is certified that error appears in the above-identified patent and that said Letters Patent is hereby corrected as shown below:

On the Title Page, Item (75), please change Inventor Jeffrey D. Hartgerink's residence from "Houston, TX" to --Pearland, TX--.

In column 1, line 23, please change "may have" to --has--.

In column 1, lines 16-18, please change "PCT/US03/04779 filed Feb. 18, 2003, entitled "SELF-ASSEMBLY OF PEPTIDE-AMPHIPHILE NANOFIBERS UNDER PHYSIOLOGICAL CONDITIONS"" to --PCT/US03/035902, filed Nov. 12, 2003, entitled COMPOSITION AND METHOD FOR SELF-ASSEMBLY AND MINERALIZATION OF PEPTIDE-AMPHIPHILES--, which is the correct PCT Application listed on the first page.

Signed and Sealed this

Seventeenth Day of November, 2009

David J. Kappos
*Director of the United States Patent and Trademark Office*